United States Patent
Karstens et al.

(10) Patent No.: US 9,174,940 B2
(45) Date of Patent: Nov. 3, 2015

(54) TSH RECEPTOR ANTAGONIZING TETRAHYDROQUINOLINE COMPOUNDS

(75) Inventors: Willem Frederik Johan Karstens, Oss (NL); Paolo Giovanni Martino Conti, Oss (NL); Cornelis Marius Timmers, Oss (NL); Ralf Plate, Oss (NL); Christianus Johannes Van Koppen, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 936 days.

(21) Appl. No.: 12/675,012

(22) PCT Filed: Aug. 28, 2008

(86) PCT No.: PCT/EP2008/061325
§ 371 (c)(1),
(2), (4) Date: Mar. 31, 2011

(87) PCT Pub. No.: WO2009/027482
PCT Pub. Date: Mar. 5, 2009

(65) Prior Publication Data
US 2011/0172267 A1    Jul. 14, 2011

(30) Foreign Application Priority Data

Aug. 31, 2007 (EP) .................................. 07115368
Jan. 18, 2008 (EP) .................................. 08150398

(51) Int. Cl.
| | |
|---|---|
| *C07D 215/38* | (2006.01) |
| *A61K 31/47* | (2006.01) |
| *A61K 31/4709* | (2006.01) |
| *C07D 401/10* | (2006.01) |
| *C07D 401/12* | (2006.01) |
| *C07D 405/12* | (2006.01) |
| *C07D 409/12* | (2006.01) |

(52) U.S. Cl.
CPC .............. *C07D 215/38* (2013.01); *A61K 31/47* (2013.01); *A61K 31/4709* (2013.01); *C07D 401/10* (2013.01); *C07D 401/12* (2013.01); *C07D 405/12* (2013.01); *C07D 409/12* (2013.01)

(58) Field of Classification Search
None
See application file for complete search history.

(56) References Cited

U.S. PATENT DOCUMENTS

| | | | | |
|---|---|---|---|---|
| 7,674,909 | B2 * | 3/2010 | Timmers et al. ............ | 546/168 |
| 7,858,794 | B2 * | 12/2010 | Timmers et al. ............ | 546/165 |
| 8,058,441 | B2 * | 11/2011 | Van Straten et al. ........ | 546/152 |
| 2004/0236109 | A1 * | 11/2004 | Van Straten et al. ........ | 546/153 |
| 2006/0142334 | A1 * | 6/2006 | Timmers et al. ............ | 514/311 |

FOREIGN PATENT DOCUMENTS

| | | |
|---|---|---|
| WO | 03/004028 A1 | 1/2003 |
| WO | 2004/056779 A2 | 7/2004 |
| WO | 2004/056779 A3 | 7/2004 |
| WO | 2004/056780 A2 | 7/2004 |
| WO | 2004/056780 A3 | 7/2004 |
| WO | 2004/113565 A1 | 12/2004 |

OTHER PUBLICATIONS

Arey, B. J. et al., "Identification and Characterization of Selective, Nonpeptide Follicle-Stimulation Hormone Receptor Antagonist", Endocrinology, 2002, p. 3822-3829, vol. 143, No. 10.
Daumerie, C. et al., "Evidence for thyrotropin receptor immunoreactivity in pretibial connective tissue from patients with thyroid-associated denmopathy", European Journal of Endocrinology, 2002, p. 35-38, vol. 146.
Evans, C. et al., "Development of a Luminescent Bioassay for Thyroid Stimulationg Antibodies", Journal of Clinical Endocrinology and Metabolism, 1999, p. 374-377, vol. 84, No. 1.
Fuhrer, D. et al., "Biological Activity of Activating Thyroid-Stimulating Hormone Receptor Mutants Depends on the Cellular Context", Endocrinology, 2003, p. 4018-4030, vol. 144, No. 9.
Gerding, M. N. et al., "Association of thyrotrophin receptor antibodies with the clinical features of Graves opthalmopathy", Clinical Endocrinology, 2000, p. 267-271, vol. 52.
Hamann, L. G. et al., "Synthesis and Biological Activity of a Novel Series of Nonsteroidal, Peripherally Selective Androgen Receptor Antagonists Derived from 1,2-Dihydropyridono(5,6-g)quinolines", J. Med. Chem. 1998, p. 623-639, vol. 41.
Kero, J. et al., "Thyrocyte-specific Gq/G11 deficiency impairs thyroid function and prevents goiter development", The Journal of Clinical Investigation, 2007, p. 2399-2407, vol. 117, No. 9.
Krohn, K. et al., "Molecular Pathogenesis of Euthyroid and Toxic Multinodular Goiter", Endocrine Reviews, 2006, p. 504-524, vol. 26, No. 4.

(Continued)

*Primary Examiner* — Ernst V Arnold
*Assistant Examiner* — Kyung Sook Chang
(74) *Attorney, Agent, or Firm* — Baerbel R. Brown; Catherine D. Fitch

(57) ABSTRACT

The present invention relates the use of a compound, a pharmaceutical composition, compounds and a kit for treating or preventing disorders in a mammal responsive to TSH receptor mediated pathways, including disorders such as hyperthyroidism, Graves' disease, Graves Ophthalmopathy, Graves' associated pretibial dermopathy, nodular goitre and thyroid cancer comprising administering to said mammal an effective amount of a tetrahydroquinoline compound of Formula (I) or an pharmaceutically acceptable salt thereof.

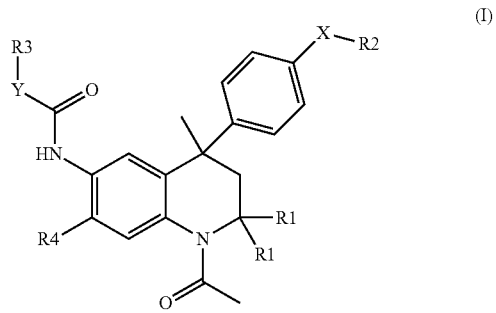

(I)

4 Claims, No Drawings

(56) References Cited

OTHER PUBLICATIONS

Manivannan, E. et al., "First QSAR report on FSH recoptor antagonistic activity: Quantitative investigations on physico-chemical and structural features among 6-amino-4-phenyltetrahydroquinoline derivatives", Bioorganic & Medicinal Chemistry Letters, 2005, p. 4496-4501, vol. 15.

Pelletier, J. C. et al., "Preparation of highly substituted-iactam follicle stimulating hormone receptor agonists", Bioorganic & Medicinal Chemistry, 2005, p. 5986-5995, vol. 13.

Schulz, A. et al., "Role of the Third Intracellular Loop for the Activation of Gonadotropin Receptors", Molecular Endocrinology, 1999, p. 181-190, vol. 13, No. 2.

Theociitou, M.E. et al., "Novel facile synthesis of 2,2,4 substituted 1,2-dihydroquinolines via a modified Skraup reation", Tetrahedron Letters, 2002, p. 3907-3910, vol. 43.

Van Sandre, J. et al., "Genetic Basis of Endocrine Disease: Somatic and Germline Mutations of the TSH Receptor Gene in Thyroid Disease", Journal of Clinical Endocrinology and Metabolism, 1995, p. 2577-2585, vol. 80, No. 9.

van Siraten, N. C. R. et al., "Identification of Substituted 6-Amino-4-phenyltetrahydroquinoline Derivatives: Potent Antagonists for the Follicle-Stimulating Hormone Receptor", J. Med. Chem., 2005, p. 1697-1700, vol. 48.

Wrobel, J. et al., "Synthesis of (bis)Suifonic Acid, (bis)Benzamides as follicle-Stimulating Hormone (FSH) Antagonists", Bioorganic & Medininal Chemistry, 2002, p. 639-656, vol. 10.

Yanofsky, S. D. et al., "Allosteric Activation of the Follicle-stimulating Hormone (FSH) Receptor by Selective, Nonpeptide Agonists", The Journal of biological Chemistry, 2006, p. 13226-13233, vol. 281, No. 19.

\* cited by examiner

TSH RECEPTOR ANTAGONIZING TETRAHYDROQUINOLINE COMPOUNDS

CROSS REFERENCE TO RELATED APPLICATION

This application is entered into national stage examination under 37 U.S.C. 371 and stems from international patent application No. PCT/EP2008/061325 filed on Aug. 28, 2008.

FIELD OF THE INVENTION

The invention relates to a compound having TSH receptor antagonist activity, in particular a tetrahydroquinoline derivative and the use thereof for the treatment and prevention of TSH receptor responsive disorders and to a pharmaceutical composition and a kit containing the same.

BACKGROUND OF THE INVENTION

Thyrotropin or thyroid-stimulating hormone (TSH) plays an important role in the regulation of metabolism and development. TSH is released from the anterior pituitary under the influence of thyrotropin—releasing hormone. It targets the thyroid gland to stimulate the release of the thyroid hormones triiodothyronine and thyroxine and thyroid growth. The actions of TSH are mediated by a specific G protein-coupled receptor which couples preferentially to Gs proteins leading to activation of adenylyl cyclase. This signal transduction pathway is predominantly responsible for the production of thyroid hormones and proliferation of the thyrocytes (Krohn et al. (2005) Endocrine Rev. 26, 504-524).

The TSH receptor on the thyroid is also directly involved in the pathogenesis and pathophysiology of Graves' disease. Graves' disease is characterized by hyperstimulation of the thyroid as a result of circulating TSH receptor-stimulating immunoglobulins (TSI), which persistently activate the receptor (Gerding et al. (2000) Clin. Endocrinol. 52, 267-271). TSI may also directly participate in the pathogenesis and pathophysiology of Graves' ophthalmopathy and Graves'-associated pretibial dermopathy as TSH receptors are present in orbital tissue and affected skin regions of these patients, respectively (Gerding et al. (2000) Clin. Endocrinol. 52, 267-271; Daumerie et al. (2002) Eur. J. Endocrinol. 146, 35-38). In addition, the TSH receptor plays a crucial role in toxic and non-toxic nodular goitre. In (toxic) nodular goitre, the thyroid gland contains autonomously functioning thyroid nodules that secrete excess thyroid hormone as a result of mutations in the TSH receptors which render them constitutively active with significantly increased cAMP levels (Krohn et al. (2005) Endocrine Rev. 26, 504-524).

Blocking the TSH receptor or inhibiting the signaling which is induced after TSH-, or TSI-mediated receptor stimulation, or as a result of constitutively active mutations of the TSH receptor will inhibit thyroid hormone secretion and thyrocyte proliferation. Low molecular weight TSH receptor antagonists could therefore be used to treat or prevent hyperthyroidism, Graves' disease, nodular goiter, Graves' ophthalmopathy and Graves'-associated pretibial dermopathy. In addition, low molecular weight TSH receptor antagonists could be used to prevent stimulation of growth of residues or metastases of thyroid cancer, which is thought to be promoted by (over)stimulation of the TSH receptor. In a more general sense, TSH receptor antagonists could be used to prevent or treat all of those ailments in which (over)activation of the TSH receptor plays a role.

Tetrahydroquinoline derivative compounds are described in WO2003/004028, WO2004/056779 and WO2004/056780. These compounds can be used to regulate fertility.

FSH receptor modulators reported in the literature have high specificity towards the FSH receptor. Yanofsky et at (2006, J. Biol. Chem. 281, 13226-13233) and Pelletier et at (2005, Bioorg. & Med. Chem. 13, 5986-5995) demonstrated that low nanomolar potent LMW FSH receptor agonists with a thiazolidinone scaffold are neither TSH recepotor antagonists nor agonists. Also (bis)sulfonic acid, (bis)benzamides, have been identified as FSH receptor antagonists, but they show no or little ability to inhibit TSH receptor activity (Wrobel et al., 2002, Biorg. Med. Chem. 10, 639-656). Another series of low micromolar FSH receptor antagonists (diazonapthylsulfonic acid derivatives) did not show affinity towards the TSH receptor (Arey et al., 2002, Endocrinology 143, 3822-3829).

In addition, mutagenesis studies on the FSH receptor and the TSH receptor have demonstrated that activation of the TSH receptor is distinct from that of the FSH receptor indicating that FSH receptor antagonists will not necessarily inhibit TSH receptor as well (Schulz et al., 1999, Mol Endocrinol 13, 181-190). This differential activation is underscored by the knowledge that the TSH receptor, in sharp contrast to the FSH receptor, also couples efficiently to phospholipase C via Gq proteins, a pathway which is required for thyroid hormone synthesis (Kero et al, 2007, J. Clin. Invest. 117, 2399-2407) and also activated by TSI in Graves' disease.

DETAILED DESCRIPTION OF THE INVENTION

The present invention describes tetrahydroquinoline compounds that inhibit TSH receptor activation. The compounds of the invention can be used as (partial) antagonists of the TSH receptor.

It has now been found, that the following class of tetrahydroquinoline compounds of formula I or pharmaceutically acceptable salts thereof, have TSH receptor antagonistic activity:

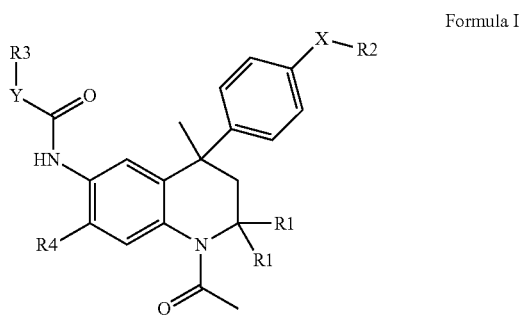

Formula I wherein
$R^1$ is H or methyl;
X is a bond, O, NH or N((1-4C)alkyl);
$R^2$ is (1-4C)alkyl, $R^5$(1-4C)alkyl or $R^9$(2-4C)alkyl,
if X is NH, $R^2$ in addition is $R^8$(1-2C)alkoxycarbonyl; or,
if X is a bond, $R^2$ in addition is H, halogen or (2-5C)heteroaryl or phenyl, both optionally substituted with one or more substituents selected from (1-3C)alkyl, (1-3C)alkoxy or halogen;
Y is a bond, O or NH, whereas
if Y is a bond, $R^3$ is phenyl, optionally one or more substituents selected from halogen, hydroxy, methoxy, phenoxy, phenyl, (1-4C)alkyl, nitro, amino or (di)[(1-4C)alkyl]amino or $R^3$ is $R^6$(1-6C)alkyl, $R^6$(3-6C)cycloalkyl, $R^7$oxy(1-6C)alkyl, or 2-pyridyl or $R^3$ is a 5-membered heteroaryl, optionally substituted with one or more substituents selected from (1-3C)alkoxy, (1-3C)alkyl or halogen;

if Y is O, $R^3$ is $R^6$(1-6C)alkyl, $R^7$oxy(2-6C)alkyl or (3-7C)cycloalkyl; and if Y is NH, $R^3$ is $R^6$(1-6C)alkyl, $R^7$oxy(2-6C)alkyl;

$R^4$ is H, (di)[(1-3C)alkyl]amino or (1-3C)alkoxy;

$R^5$ is CN or pyridyl;

$R^6$ is H, or (3-5C)cycloalkyl, (2-5C)heteroaryl or phenyl, the latter three groups optionally substituted with one or more substituents selected from halogen, (1-4C)alkoxy or (1-4C)alkyl, the latter two optionally substituted with one or more halogen;

$R^7$ is (2-5C)heteroaryl or phenyl, both optionally substituted with one or more substituents selected from halogen, (1-4C)alkoxy or (1-4C)alkyl;

$R^8$ is H or (2-5C)heteroaryl or phenyl, both optionally substituted with one or more substituents selected from (1-3C)alkyl, (1-3C)alkoxy or halogen; and $R^9$ is (di)[(1-4C)alkyl]amino or (2-6C)heterocycloalkyl.

In the above Formula 1, the two $R^1$ groups are always the same and are either H or methyl.

In particular, the compounds of the present invention show antagonistic TSH receptor activity.

Thus, the TSH receptor antagonistic compounds of the present invention may be used to treat a mammal, including a human, with disorders responsive to TSH receptor mediated pathways. They can also be used to prevent such TSH receptor mediated disorders. The TSH receptor antagonistic compounds of the present invention also fully inhibit TSH receptor-mediated phospholipase C activity with equal potency.

The following terms are intended to have the indicated meanings denoted below as used in the specification and claims.

The term (1-3C)alkyl as used in the definition means a branched or unbranched alkyl group having 1-3 carbon atoms, being methyl, ethyl, propyl or isopropyl.

The term (1-4C)alkyl as used in the definition means a branched or unbranched alkyl group having 1-4 carbon atoms, being methyl, ethyl, propyl, isopropyl, butyl, isobutyl, sec-butyl and tert-butyl.

The term (2-4C)alkyl as used in the definition means a branched or unbranched alkyl group having 2-4 carbon atoms, being, ethyl, propyl, isopropyl, butyl, isobutyl, sec-butyl and tert-butyl.

The term (1-6C)alkyl as used in the definition means a branched or unbranched alkyl group having 1-6 carbon atoms for example methyl, ethyl, propyl, isopropyl, butyl, tert-butyl, n-pentyl and n-hexyl. (1-5C)Alkyl groups are preferred.

The term (2-6C)alkyl as used in the definition means a branched or unbranched alkyl group having 2-6 carbon atoms such as ethyl, propyl, isopropyl, butyl, penty or hexyl.

The term (3-6C)cycloalkyl means a cycloalkyl group having 3-6 carbon atoms, being cyclopropyl, cyclobutyl, cyclopentyl and cyclohexyl.

The term (3-5C)cycloalkyl means a cycloalkyl group having 3-5 carbon atoms, being cyclopropyl, cyclobutyl and cyclopentyl.

The term (3-7C)cycloalkyl means a mono or bicycloalkyl group having 3-7 carbon atoms, such as cyclopropyl, cyclobutyl, cyclopentyl, cyclohexyl and norbonyl.

The term (2-5C)heteroaryl means an aromatic group having 2-5 carbon atoms and at least including one heteroatom selected from N, O and/or S. More than one heteroatom, including different heteroatoms may be included if feasible. Preferred heteroaryl groups are thienyl, furyl, pyridyl, isoxazolyl, pirimidyl, pyrrolyl. The (2-5C)heteroaryl group may be attached via a carbon atom or a heteroatom, if feasible.

The term 5-membered heteroaryl means an aromatic group having 2-4 carbon atoms and at least including one heteroatom selected from N, O and/or S. More than one heteroatom, including different heteroatoms may be included if feasible. Preferred heteroaryl groups are thienyl, furyl, imidazalolyl, isoxazolyl, pirazolyl, pyrrolyl, oxadiazolyl, oxazolyl or thiazolyl. The 5-membered heteroaryl group may be attached via a carbon atom or a heteroatom, if feasible.

The term (1-3C)alkoxy means an alkoxy group having 1-3 carbon atoms, the alkyl moiety having the same meaning as previously defined.

The term (1-4C)alkoxy means an alkoxy group having 1-4 carbon atoms, the alkyl moiety having the same meaning as previously defined. (1-2C)Alkoxy groups are preferred.

The term (1-2)alkoxycarbonyl means carbonyl group with an attached alkoxy group having 1-2 carbon atoms.

The term (2-6C)heterocycloalkyl means a heterocycloalkyl group, having 2-6 carbon atoms and at least including one heteroatom selected from N, O and/or S, which may be attached via a heteroatom, if feasible, or a C atom. More than one heteroatom, including different heteroatoms may be included if feasible. The preferred number of heteroatoms is 1-2. The preferred number of C-atoms is 3-6. Preferred groups are morpholinyl, homomorpholinyl, piperidinyl and homopiperidinyl. Most preferred is morpholinyl.

The term oxy(1-6C)alkyl means an oxyalkyl group having 1-6 carbon atoms, the alkyl moiety having the same meaning as previously defined.

The term oxy(2-6C)alkyl means an oxyalkyl group having 2-6 carbon atoms, the alkyl moiety having the same meaning as previously defined.

The term (di)[(1-4C)alkyl]amino as used herein means an amino group, monosubstituted or disubstituted with alkyl groups, each of which contains 1-4 carbon atoms and has the same meaning as previously defined.

The term (di)[(1-3C)]alkylamino as used herein means an amino group, monosubstituted or disubstituted with alkyl groups, each of which contains 1-3 carbon atoms and has the same meaning as previously defined.

The term halogen means fluorine, chlorine, bromine or iodine.

The term pharmaceutically acceptable salt represents those salts which are, within the scope of medical judgement, suitable for use in contact for the tissues of humans and/or animals without undue toxicity, irritation, allergic response and the like, and are commensurate with a reasonable benefit/risk ratio. Pharmaceutically acceptable salts are well known in the art.

The compounds of the present invention possess at least one chiral carbon atom and may therefore be obtained as pure enantiomers, or as a mixture of enantiomers, or as a mixture of diastereomers.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

Another aspect of the present invention relates to the compounds and the use of compounds of Formula I wherein Y is a bond, O or NH, whereas if Y is a bond, $R^3$ is phenyl, optionally mono/di substituted with halogen, hydroxy, methoxy, phenoxy, phenyl, (1-4C)alkyl, nitro, amino or (di)[(1-4C)alkyl]amino or $R^3$ is $R^6$(1-6C)alkyl, $R^6$(3-6C)cycloalkyl, $R^7$oxy(1-6C)alkyl, or 2-pyridyl or $R^3$ is a 5-membered heteroaryl, optionally substituted with (1-3C)alkoxy, (1-3C)alkyl or halogen;

if Y is O, $R^3$ is $R^6$(1-6C)alkyl or $R^7$oxy(2-6C)alkyl; and if Y is NH, $R^3$ is $R^6$(2-6C)alkyl, $R^7$oxy(2-6C)alkyl;

wherein Y is a bond, O or NH, whereas if Y is O, $R^3$ is $R^6$(1-6C)alkyl or $R^7$oxy(2-6C)alkyl and wherein if Y is NH and $R^3$ is $R^6$(2-6C)alkyl or $R^7$oxy(2-6C)alkyl.

Another aspect of the present invention relates to the compounds and the use of compounds of Formula I wherein X is a bond or O.

Yet another aspect of the invention relates to the compounds and the use of compounds of Formula I wherein $R^2$ is H and X is a bond.

Another aspect of the invention relates to the compounds and the use of compounds according to Formula I wherein $R^2$ is $R^5$(1-4C)alkyl and X=O.

The present invention also provides for the compounds and the use of compounds according to Formula I wherein $R^4$ is H, or (di)[(1-3C)alkyl]amino.

The invention also provides the compounds and the use of compounds according to Formula I wherein X is a bond, O or NH.

The invention also relates to compounds and use of compounds according to Formula I which are enantiomers showing the (+) optical rotation.

Yet another aspect of the invention concerns the compounds and use of compounds wherein all specific definitions of the groups $R^1$ through R9 and X and Y as defined here above are combined in the compound of formula I.

Suitable methods for the preparation of the compounds of the invention are outlined below.

If R1=Me, the compounds of general formula I can be prepared starting with the well-documented Skraup reaction. Performing this reaction on N-tert-butoxycarbonyl (N-Boc) protected 1,4-phenylenediamine 1 gives 1,2-dihydroquinoline derivative 2. The above mentioned reaction is typically conducted at elevated temperature in acetone or mesityl oxide in the presence of iodine or protic acid such as hydrochloric acid, p-toluenesulfonic acid or aqueous hydrogen iodide. Alternatively, compound 2 can be prepared by reacting compound 1 with acetone in the presence of $MgSO_4$, 4-tert-butylcatechol and iodine (L. G. Hamann, R. I. Higuchi, L. Zhi, J. P. Edwards and X.-N. Wang, J. (1998) Med. Chem. 41, 623-639). In yet another procedure, the reaction can be performed in acetone using lanthanide triflates (e.g. scandium triflate) as catalysts. In this case, the reaction can be run at room temperature or at elevated temperatures using conventional heating or microwave irradiation (M. E. Theoclitou and L. A. Robinson (2002) Tetrahedron Lett. 43:3907-3910).

Subsequent 1-N-acetylation of compound 2 can be carried out using standard conditions. Compound 2 can be acylated in a solvent such as tetrahydrofuran, with acetyl chloride in the presence of a base such as pyridine to give 1-N-acetyl-4-methyl-1,2-dihydroquinoline 3.

Cleavage of the Boc protective group under conditions well known to those skilled in the art affords 6-amino-1,2-dihydroquinoline 4. This reaction is typically conducted in dichloromethane in the presence of trifluoroacetic acid.

Introduction of the requisite substituted phenyl group at position 4 of the dihydroquinoline scaffold can be accomplished via Friedel-Crafts alkylation of benzene, anisole or bromobenzene with compound 4 to yield compounds of general formula 5.

This reaction is conducted at ambient or elevated temperatures in benzene, anisole or bromobenzene under catalysis of a Lewis acid (e.g. $AlCl_3$).

Subsequent 6-N-functionalisation of the compounds of general formula 5 can be carried out using standard conditions to give the compounds of general formula 6, wherein R3 is as previously defined. For example, compounds of formula 5 may react in a solvent such as dichloromethane, tetrahydrofuran or toluene with an acyl halide (R3-C(O)-hal, where hal=Cl, Br or I) in the presence of a base such as N,N-diisopropylethylamine or pyridine. Alternatively, acylation can be accomplished by reaction with an appropriate carboxylic acid (R3-$CO_2$H) in the presence of a coupling reagent such as O-(benzotriazol-1-yl)-N,N,N',N'-tetramethyluronium tetrafluoroborate (TBTU) or O-(7-azabenzotriazole-1-yl)-N,N,N',N'-tetramethyluronium hexafluorophosphate (HATU) and a tertiary base, e.g. N,N-diisopropylethylamine, in a solvent such as N,N-dimethylformamide or dichloromethane at ambient or elevated temperature. Furthermore, compounds of general formula 5 can be converted to carbamates 6b or ureas 6c via the isocyanate 7. In a typical reaction, compound 5 is converted into the isocyanate 7 in a solvent such as ethyl acetate with trichloromethyl chloroformate in the presence of activated carbon at elevated temperature. The isocyanate 7 can be converted with the appropriate alcohols R3-OH into carbamates 6b (wherein R3 is as previously defined) or with the appropriate amines R3-$NH_2$ into ureas 6c (wherein R3 is as previously defined) in a solvent such as tetrahydrofuran or dichloromethane in the presence of a base such as triethyl amine or N,N-diisopropylethylamine at ambient or elevated temperature. Alternatively, compounds of general formula 5 can be converted in a solvent such as tetrahydrofuran, dichloromethane or N,N-dimethylformamide with appropriate chloroformates R3-O—C(O)—Cl or isocyanates R3-N=C=O into carbamates 6b or ureas 6c respectively, wherein R3 is as previously defined, at ambient or elevated temperature.

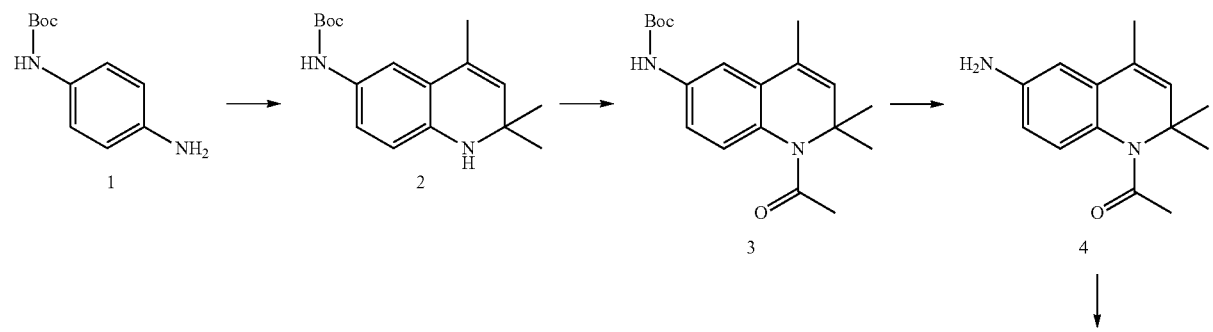

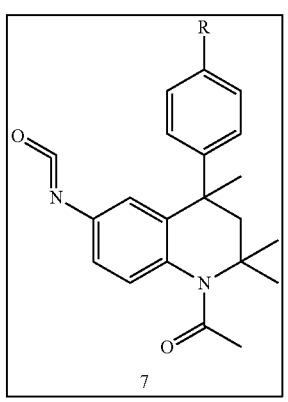
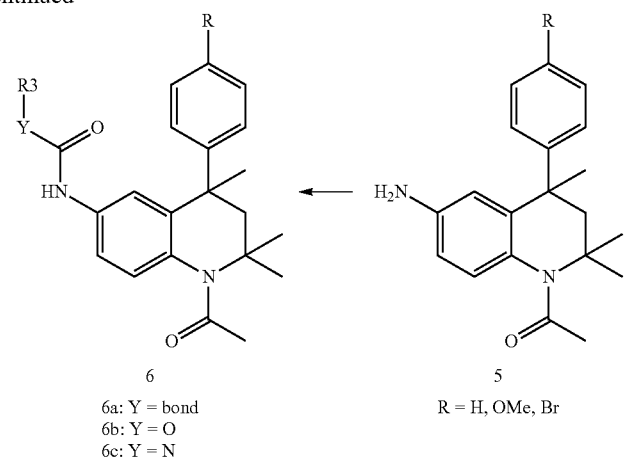

If R1=H, the compounds of general formula I can be prepared starting with a Wittig reaction. Performing this reaction with a ketone of general formula 8 with (diethoxy-phosphoryl)-acetic acid ethyl ester yields the α,β-unsaturated esters of general formula 9 which can be converted to the carboxylic acids of general formula 10 by sodium hydroxide (2N) in ethanol at room temperature.

Subsequent acylation of aniline with acids of general formula 10 can be carried out using standard conditions to give compounds of general formula 11. Acylation can be accomplished in the presence of a coupling reagent such as O-(benzotriazol-1-yl)-N,N,N',N'-tetramethyluronium tetrafluoroborate (TBTU) or O-(7-azabenzotriazole-1-yl)-N,N,N',N'-tetramethyluronium hexafluorophosphate (HATU) and a tertiary base, e.g. N,N-diisopropylethylamine, in a solvent such as N,N-dimethylformamide or dichloromethane at ambient or elevated temperature.

The ring closure of compounds of general formula 11 can be performed with concentrated $H_2SO_4$ at room temperature yielding compounds of the general formula 12 which can be subsequently reduced using $BH_3$—$S(CH_3)_2$ in toluene at elevated temperature to yield tetrahydroquinolines of general formula 13.

Compounds of general formula 13 can be acetylated using standard conditions. In a typical experiment, compounds of general formula 13 are reacted in a solvent such as dichloromethane or tetrahydrofuran with acetyl chloride in the presence of a base such as triethylamine or pyridine to give compounds of general formula 14.

Introduction of the nitro-group at position 6 of the tetrahydroquinolines 14 can be accomplished by using a mixture of nitric acid and acetic anhydride in dichloromethane as the solvent at room temperature. The obtained compounds of general formula 15 can be converted to the aniline derivatives 16, by a reduction using zinc in the presence of acetic acid and tetrahydrofuran as the solvent at 0° C.

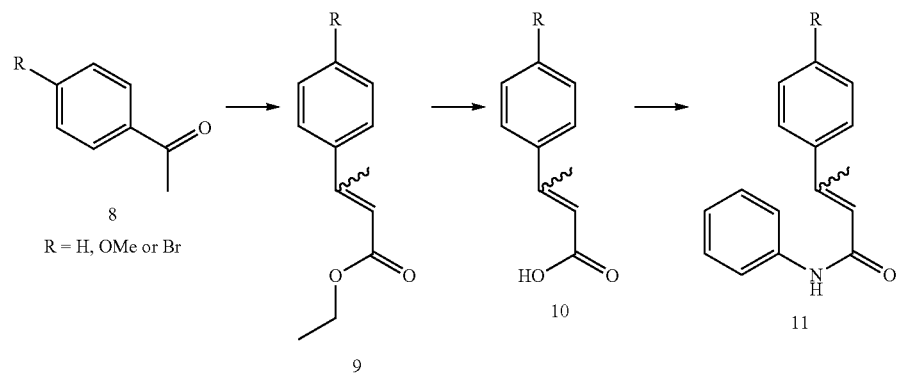

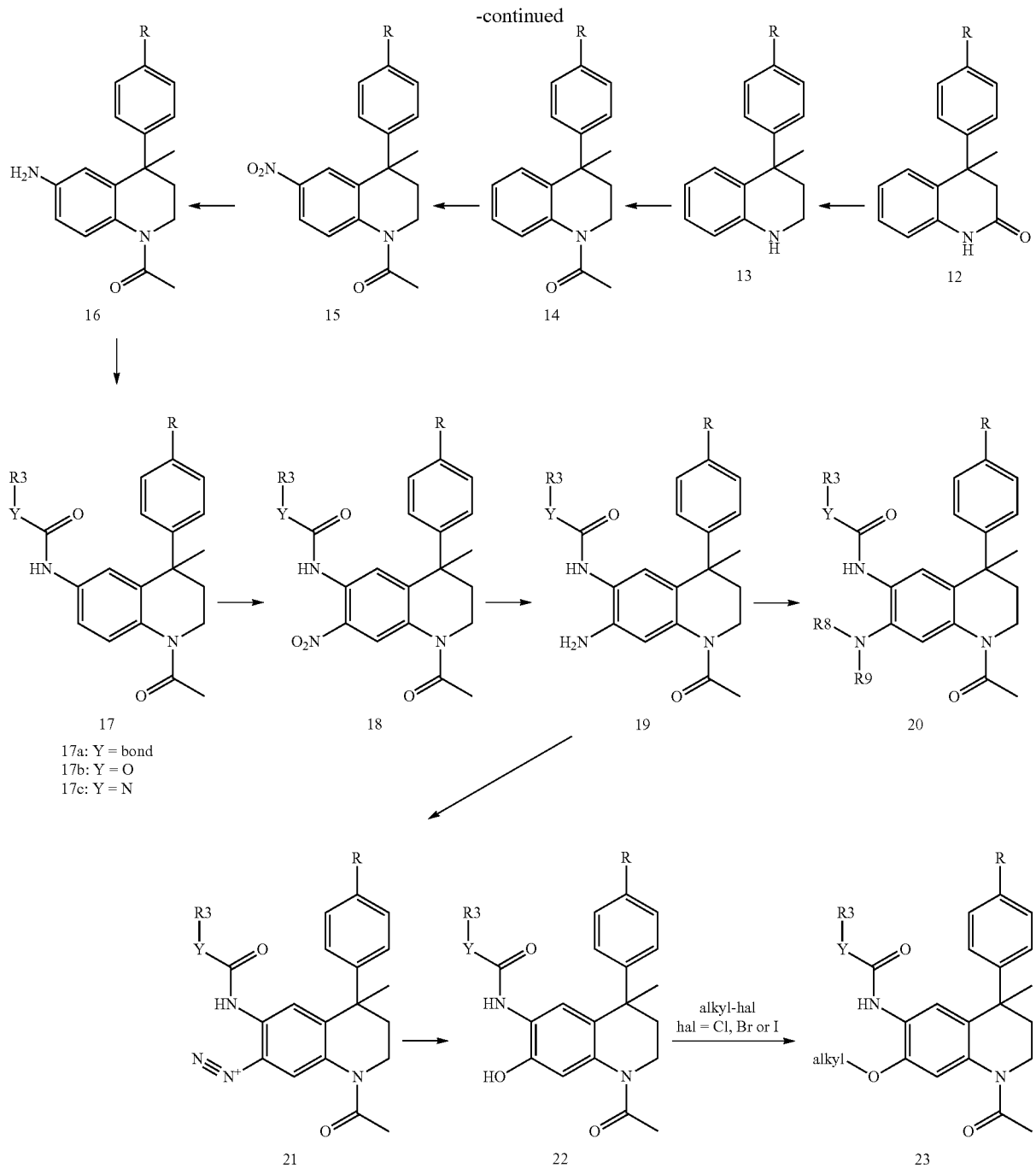

Subsequent 6-N-acylation of the compounds of general formula 16, to give the compounds of general formula 17a, wherein R3 is as previously defined can be carried out using standard conditions, as described for the acylation of compounds of the general formula 5. Similarly, carbamates 17b, wherein R3 is as previously defined, and ureas 17c, wherein R3 is as previously defined, can be prepared, starting from compounds of general formula 16, as described for carbamates 6b and ureas 6c.

Furthermore, compounds of general formula 20 and 23 can be prepared as described for compounds of general formula 30 and 33 respectively, starting from compounds of general formula 17.

Compounds of general formula 17 and 6 (if R=Br) can be converted via a Suzuki reaction with boronic acids or boronic esters into compounds of general formula 24. In a typical experiment, a bromide of general formula 17 or 6 can react with a boronic acid or boronic ester in a solvent such as dimethoxyethane or dioxane using cesium fluoride or potassium phosphate as a base and a palladium catalyst, such as palladium tetrakistriphenylphosphine or palladium dichloroditriphenylphosphine, in the presence of triphenylphosphine or triphenylarsine at elevated temperature. Furthermore, compounds of general formula 17 and 6 (if R=Br) can be converted via Buchwald chemistry into the anilines of general formula 25. Compounds of general formula 17 or 6 may react in dimethoxyethane with benzophenone imine in the presence of sodium tert-butoxide as a base, tris(dibenzylideneacetone)dipalladium as a catalyst and 2,2'-bis(diphenylphosphino)-1,1'-binaphthyl at elevated temperature followed by a hydrolysis with aqueous hydrochloric acid in tetrahydrofuran at ambient temperature to give the aniline derivatives of general formula 25.

Alkylation of compounds of general formula 25, yielding compounds of general formula 27a wherein R2 is as previously defined, can be carried out using the appropriate alkyl halides (R2-hal, wherein hal=Cl, Br or I) in a solvent such as ethanol, tetrahydrofuran or N,N-dimethylformamide with a base such as triethyl amine, potassium carbonate, cesium carbonate or sodium bicarbonate in the presence of sodium iodide or potassium iodide as a catalyst. Furthermore, compounds of general formula 25 can be converted to carbamates of general formula 27b via the isocyanates of general formula 26. In a typical reaction, compounds of general formula 25 are converted into the isocyanates of general formula 26 in a solvent such as ethyl acetate with trichloromethyl chloroformate in the presence of activated carbon at elevated temperature. The isocyanates of general formula 26 can be converted into carbamates of general formula 27b, wherein R2 is as previously defined, in a solvent such as tetrahydrofuran or dichloromethane with the appropriate alcohol in the presence of a base such as triethyl amine or N,N-diisopropylethylamine. Alternatively, compounds of general formula 25 can be converted into carbamates of general formula 27b, wherein R2 is as previously defined, in a solvent such as tetrahydrofurane, dichloromethane or N,N-dimethylformamide with an appropriate chloroformate at ambient or elevated temperature.

Introduction of the nitro-group onto compounds of general formula 27 can be accomplished via a nitration using a mixture of (fuming) nitric acid and glacial acid in dichloromethane or concentrated sulfuric acid at ambient temperature or elevated temperature to yield compounds of general formula 28. The aniline derivatives 29 can be obtained via a reduction of compounds of general formula 28 with zinc in tetrahydrofuran in the presence of glacial acetic acid at ambient or elevated temperature. The primary amine function in compounds of general formula 29 can be converted into alkylated anilines of general formula 30 via a reductive alkylation with aliphatic aldehydes in methanol using sodium cyanoborohydride in the presence of glacial acetic acid.

Furthermore, compounds of general formula 29 can be converted into alcohols of general formula 32 via the diazonium salts of general formula 31 by using methods well known to those skilled in the art. In a typical experiment, compounds of general formula 29 react in a solvent such as water with NaNO$_2$ and H$_2$SO$_4$ followed by addition of urea, Cu(NO$_3$)$_2$ and Cu$_2$O at 0° C. or ambient temperature to yield the alcohols of general formula 32.

Alkylation of compounds of general formula 32 can be carried out using alkyl halides in a solvent such as ethanol, tetrahydrofuran or N,N-dimethylformamide with a base such as triethyl amine, potassium carbonate, cesium carbonate or sodium bicarbonate in the presence of sodium iodide or potassium iodide as a catalyst to yield compounds of general formula 33.

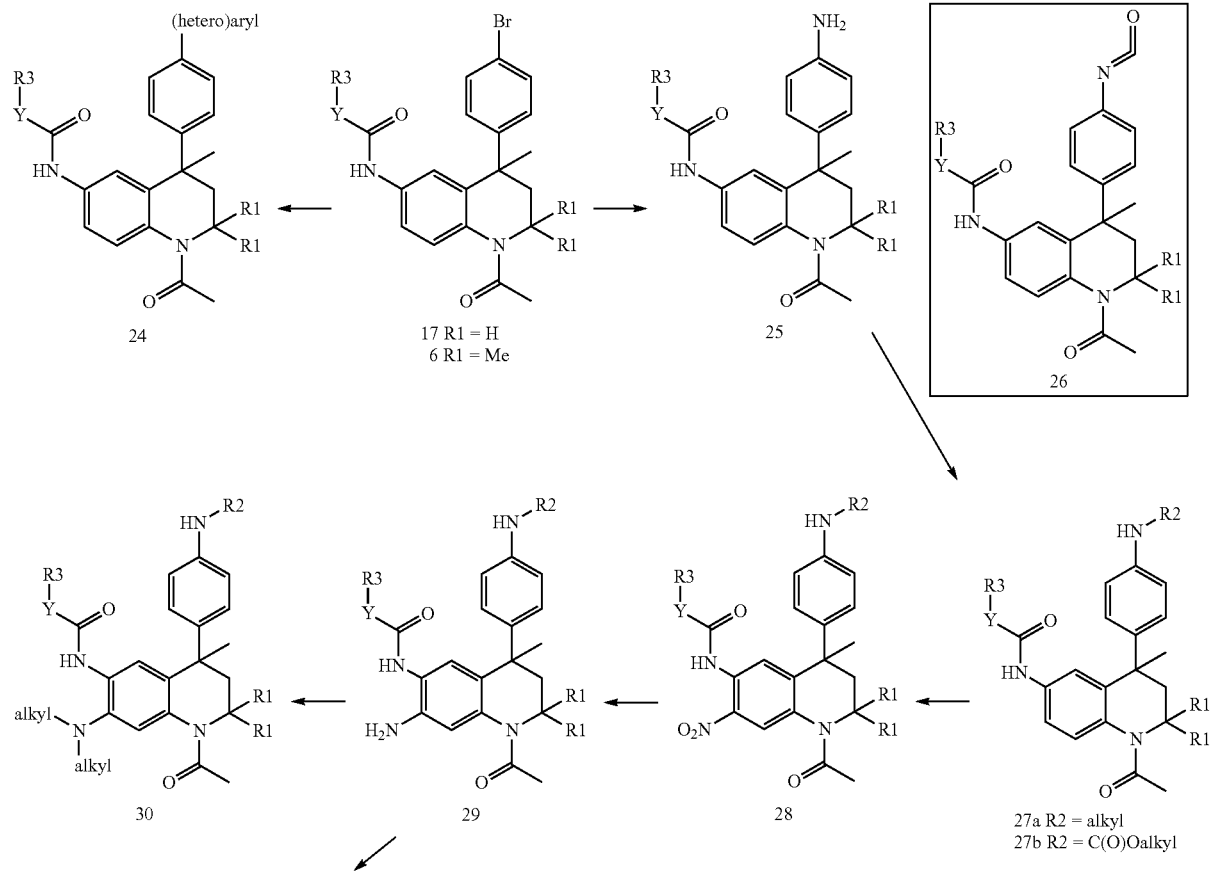

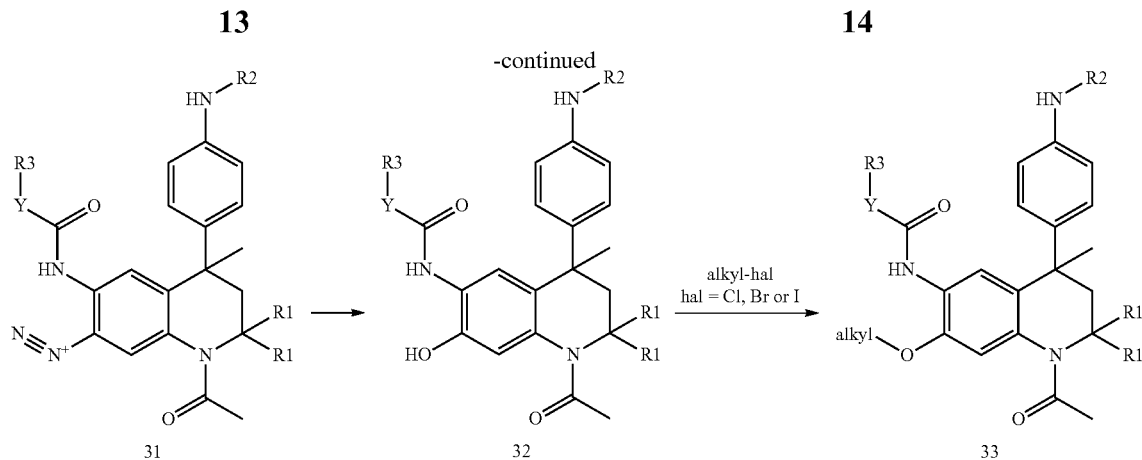

A procedure to obtain compounds of general formula 39 starts with the conversion of compounds of general formula 5 or 16 with 9-fluorenylmethyl chloroformate (Fmoc-Cl) in dichloromethane in the presence of triethyl amine at 0° C. to give compounds of general formula 34.

Subsequent introduction of the nitro-group can be accomplished via a nitration using a mixture of fuming nitric acid and glacial acid in dichloromethane at ambient temperature to yield compounds of general formula 35. The aniline derivatives 36 can be obtained via a reduction of compounds 35 with zinc in tetrahydrofuran in the presence of glacial acetic acid at ambient temperature. The primary amine function in compounds 36 can be converted into alkylated anilines of general formula 37 via a reductive alkylation with aliphatic aldehydes in methanol using sodium cyanoborohydride in the presence of glacial acetic acid. The Fmoc-group removal can be accomplished with piperidine in dichloromethane to give the aniline derivatives of general formula 38.

Subsequent 6-N-acylation of the compounds of general formula 38 can be carried out using standard conditions, as described for the acylation of compounds of general formula 5, to give the compounds of general formula 39a, wherein R3 is as previously defined. Similarly, carbamates 39b, wherein R3 is as previously defined, and ureas 39c, wherein R3 is as previously defined, can be prepared, starting from compounds of general formula 38, as described for carbamates 6b and ureas 6c.

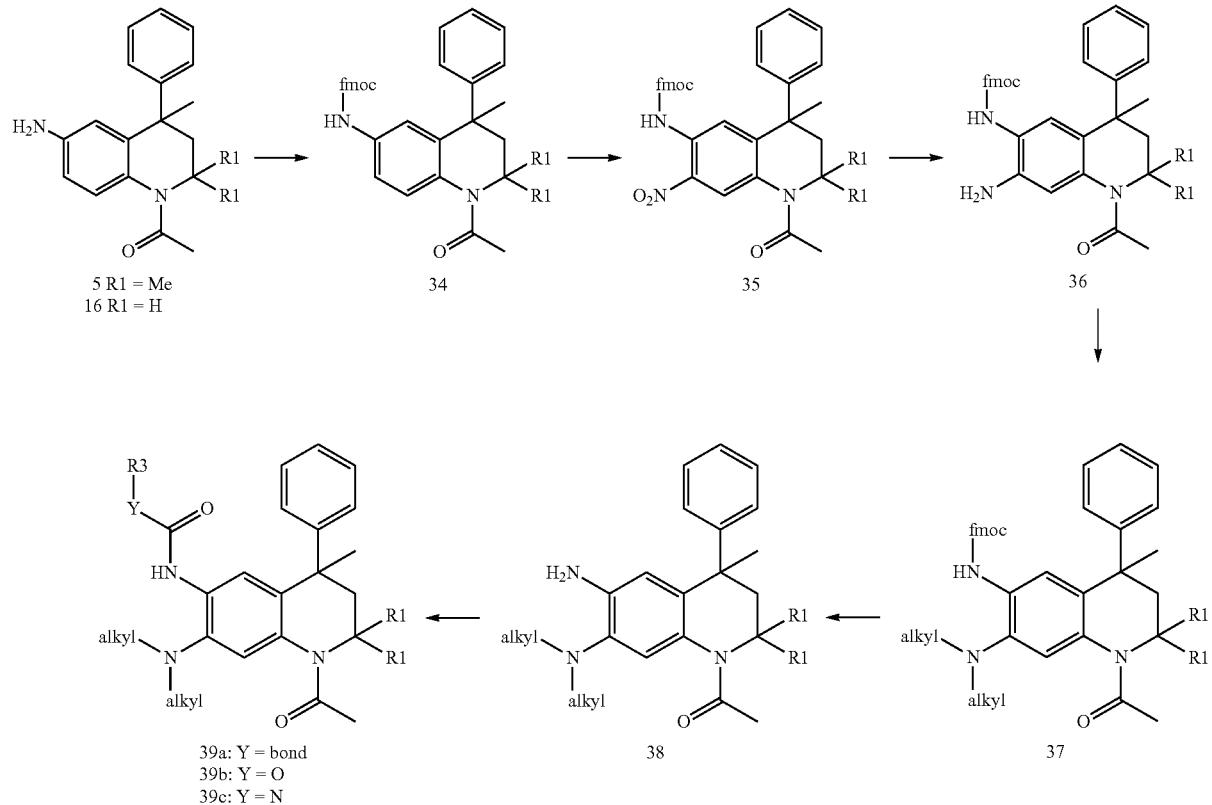

Alternatively, compounds of general formula 39 can be prepared starting from compounds of general formula 35. The Fmoc-group removal can be accomplished with piperidine in dichloromethane to give the aniline derivatives of general formula 40.

Subsequent 6-N-functionalization of compounds of general formula 40 can be carried out using standard conditions, as described for the preparation of compounds of general formula 6, to give compounds of general formula 41, wherein R3 is as previously defined. The aniline derivatives 42 can be obtained via a reduction of compounds 41 with zinc in tetrahydrofuran in the presence of glacial acetic acid at ambient temperature. The primary amine function in compounds 42 can be converted into alkylated anilines of general formula 39 via a reductive alkylation with aldehydes in methanol using sodium cyanoborohydride in the presence of glacial acetic acid.

derivative 46 can be prepared via the previously mentioned Skraup reaction followed by N-acylation using acetyl chloride in pyridine/dichloromethane (1/1) as the solvent in the presence of N,N-dimethyl aniline to yield compound 47. The Fmoc-group removal can be accomplished with piperidine in dichloromethane to give the aniline derivative 48. Modification of the 6-amino group to amides 49a, carbamates 49b and ureas 49c, can be performed using conditions as mentioned for the preparation of compounds of general formula 6.

Introduction of the phenyl group at position 4 of the dihydroquinoline scaffold can be accomplished via Friedel-Crafts alkylation of benzene with the compounds of general formula 49. This reaction is conducted at ambient or elevated temperatures in benzene, under catalysis of a Lewis acid (e.g. AlCl₃). Under these conditions demethylation takes place to yield compounds of general formula 50. Compounds of gen-

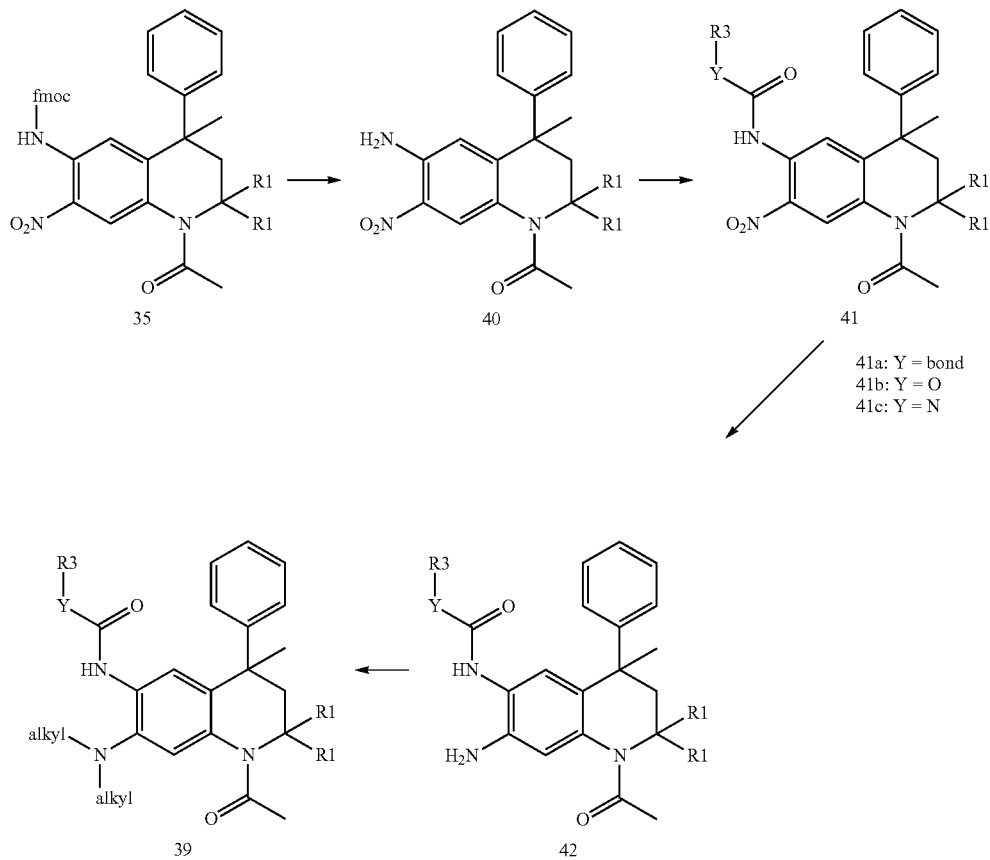

A procedure to obtain compounds of general formula 51 and 52 starts with the reaction of compound 43 with 9-fluorenylmethyl chloroformate (Fmoc-Cl) in tetrahydrofuran in the presence of pyridine at 0° C. to give compound 44. The aniline derivative 45 can be obtained via a reduction of compound 44 with zinc in tetrahydrofuran in the presence of glacial acetic acid at ambient temperature. Dihydroquinoline eral formula 52 can be obtained if the reaction is carried out in anisole.

Alcohols of general formula 50 can be alkylated using alkyl halides in a solvent such as acetonitrile, tetrahydrofuran or N,N-dimethylformamide in the presence of a base such as potassium carbonate, potassium tert-butoxide or sodium hydride to yield the compounds of general formula 51.

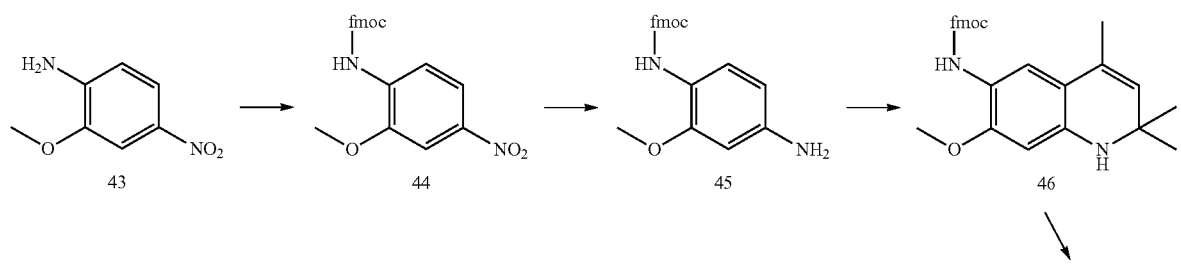

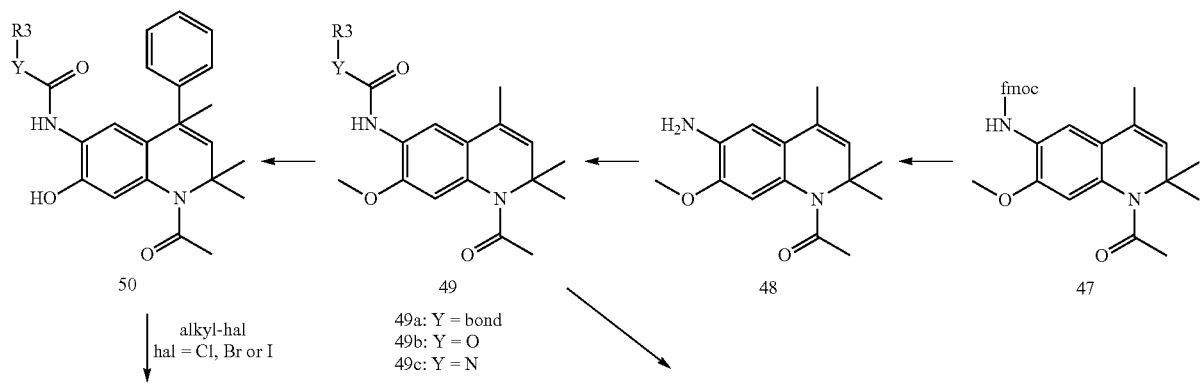

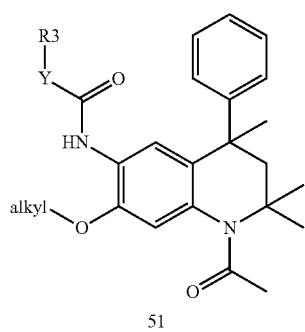

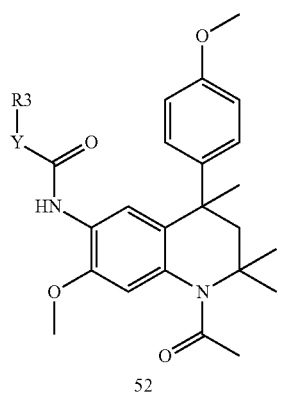

A procedure to obtain compounds of general formula 54 and 57 starts with the demethylation of compounds with general formula 6 or 17 where R=OMe. If R=OMe, demethylation can be effected in a solvent such as dichloromethane in the presence of boron tribromide ($BBr_3$) at ambient or elevated temperature to yield alcohols of general formula 53. Alkylation of compounds of general formula 53 can be carried out using alkyl halides (R2-hal) in a solvent such as ethanol, tetrahydrofuran or N,N-dimethylformamide with a base such as triethyl amine, potassium carbonate, cesium carbonate or sodium bicarbonate in the presence of sodium iodide or potassium iodide as a catalyst to yield compounds of general formula 54. Introduction of the nitro-group onto compounds of general formula 54 to yield compounds of general formula 55, followed by nitro group reduction to compounds of general formula 56 and amino alkylation to yield compounds of general formula 57 can be accomplished using conditions as described for the conversion of compounds of general formula 27 into compounds of general formula 30.

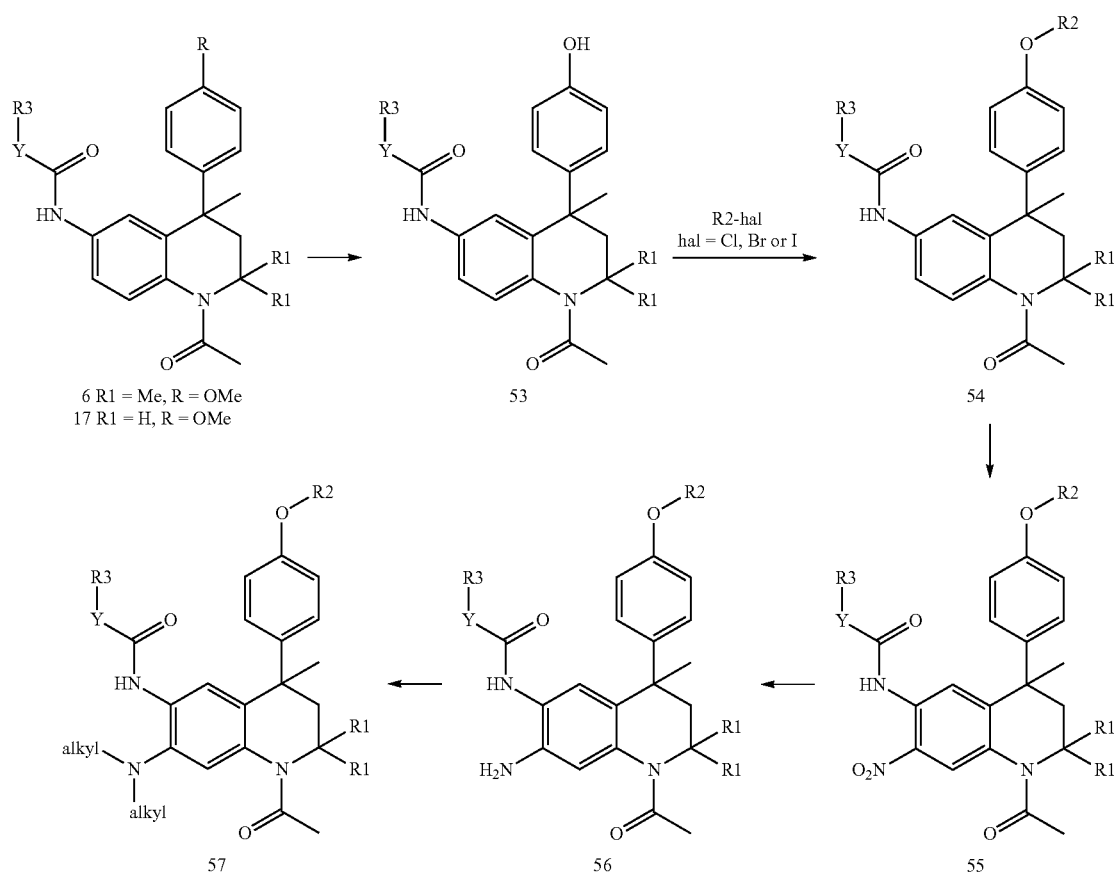

Additionally suitable methods for the preparation of some compounds of the invention are described in WO2004/056779 and WO2004/056780.

Some of the compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

Methods for obtaining the pure enantiomers are well known in the art, e.g crystallization of salts which are obtained from optically active acids and the racemic mixture, or chromatography using chiral columns. For diastereomers, straight phase or reversed phase columns may be used. Optical rotation can easily be measured e.g. with a polarimeter.

The compounds of the present invention inhibit the TSH receptor. The skilled artisan will recognize that desirable $IC_{50}$ values are dependent on the compound tested. For example, a compound with an $IC_{50}$ value of less than 1E-5 M is generally considered a candidate for drug selection. In general, the $IC_{50}$ values are preferably lower than 1E-7 M. However, a compound which has a larger $IC_{50}$ value but is more selective for the particular receptor may be even a better candidate. The compounds of the present invention might also possess FSH receptor activity but they do not have a FSH receptor selectivity over the TSH receptor. Generally it can be stated that the compounds of the present invention have high TSH receptor activity and are at least equipotent on FSH and TSH receptors.

Methods to determine receptor binding, as well as in vitro and in vivo assays to determine biological activity of thyrotropin or the TSH receptor are well known. In the in vitro assays, the expressed TSH receptor is incubated with the test compound and receptor binding or stimulation/inhibition of a functional response is measured. Ex vivo human or animal thyrocytes/thyroid slices or thyroid cell lines may be used (Fuhrer et al. (2003) Endocrinology 144, 4018-4030). Alternatively, cDNA encoding the TSH receptor may heterologously be expressed in suitable host cells, e.g. Chinese Hamster Ovary cells, but other cell lines, preferably of mammalian origin, are also suitable (Fuhrer et al. (2003) Endocrinology 144, 4018-4030). Methods to construct cells expressing recombinant TSHR are well known in the art.

Techniques for site-directed DNA mutagenesis, DNA ligation, PCR and construction of suitable expression systems are all well known in the art. Portions, or all, of the DNA encoding the desired receptor can be constructed synthetically using standard solid phase techniques, preferably to include restriction sites for ease of ligation. Suitable control elements for transcription and translation of the inserted coding sequence can be ligated to the DNA coding sequence. As is well known, expression systems are available, which are compatible with a wide variety of hosts, including bacteria and eukaryotic hosts such as yeast, insect cells, avian, mammalian cells and the like.

Cells expressing the TSH receptor are incubated with the test compound to observe binding, stimulation or inhibition of a functional response. Alternatively, isolated cell membranes containing the expressed receptor may be used to determine binding of test compound. For measurement of binding, radioactively labeled or fluorescently labeled compounds may be used. Also competitive binding assays can be performed. Another biochemical assay involves the screening for TSH receptor-mediated cAMP accumulation. Such an assay involves incubation of the TSH receptor-expressing cells with the test compound for a sufficient period of time and measurement of cAMP, often in the presence of a cAMP phosphodiesterase inhibitor to block cAMP degradation. The amount of cAMP can be decreased or increased, depending on the inhibitory or stimulating effect of the test compound upon binding to the receptor. Screening for TSH receptor antagonists involves incubation of the TSH receptor expressing cells with a concentration range of test compound in the presence of a fixed, submaximally effective TSH concentration (i.e., a TSH concentration that induces approximately 80% of the maximal stimulation of cAMP accumulation in the absence of compound). Instead of TSH, serum from Graves' disease patients, or (partially) purified TSI can be used to stimulate the TSH receptor (Gerding et al. (2000) Clin. Endocrinol. 52, 267-271). Alternatively, constitutively active TSH receptors can be heterologously expressed and the antagonistic effect of test compounds on the active receptor may result in reduction in the increased basal cAMP levels (Fuhrer et al. (2003) Endocrinology 144, 4018-4030). From the concentration-effect curves, the IC50 value and the percentage of inhibition of TSH receptor-induced cAMP accumulation can be determined for each of the test compounds.

In addition to a direct measurement of cAMP, cell lines can be used, which in addition to transfection with receptor cDNA are also transfected with a second cDNA encoding a reporter gene, which expression is dependent on the intracellular level of cAMP. Such reporter genes might be cAMP-inducible or might be constructed in such a way that they are connected to novel cAMP responsive elements. In general, reporter gene expression might be controlled by any response element reacting to changing levels of cAMP. Suitable reporter genes are e.g. the genes encoding firefly luciferase, beta-galactosidase, alkaline phosphatase or beta-lactamase. The principles of such transactivation assays are well known in the art and are described, e.g. in Evans et al. (1999) J. Clin. Endocrinol. Metab. 84, 374-377. As reference compound human (recombinant) TSH or bovine TSH can be used.

The present invention also relates to a pharmaceutical composition comprising a tetrahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, ocular, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

For an ophthalmic formulation, the active ingredient may be presented as a solution, suspension, ointment, or gel for application on the conjunctiva or cornea, or for retrobulbar injection.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as herein described.

Thus, the present invention also provides a kit to treat disorders responsive to TSH receptor mediated pathways.

The kits comprise: A) a pharmaceutical composition comprising a compound of Formula I or a pharmaceutically acceptable salt thereof; and B) instructions describing a method of using the pharmaceutical composition to treat disorders responsive to TSH receptor mediated pathways.

In another aspect the kit can be used to prevent disorders responsive to TSH receptor mediated pathways.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material The tetrahydroquinoline derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO Nobel N. V.).

The exact dose and regimen of administration of the active ingredient, or a pharmaceutical composition thereof, will necessarily be dependent upon the therapeutic effect to be achieved, and may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-25mg per kg body weight. The desired dose may be presented as one dose or as multiple subdoses administered at appropriate intervals throughout the day.

A further aspect of the invention resides in the use of a tetrahydroquinoline derivative compound having the general formula I as described hereinabove for the manufacture of a medicament to be used for the treatment of disorders responsive to TSH receptor mediated pathways. Thus, patients in need thereof can be administered with suitable amounts of the compounds according to the invention.

In another aspect the invention resides in the use of a tetrahydroquinoline derivative compound having the general formula I for the manufacture of a medicament to be used for the treatment of patients with a need to inhibit the actions of TSH, TSI or constitutive activity of TSH receptors.

In another aspect the invention resides in the use of a tetrahydroquinoline derivative compound having the general formula I for the treatment of hyperthyroidism.

In yet another aspect the invention resides in the use of a tetrahydroquinoline derivative compound having the general formula I for the treatment of Graves' disease.

In still another aspect the invention resides in the use of a tetrahydroquinoline derivative compound having the general formula I for the treatment of Graves' ophthalmopathy.

Another aspect of the invention resides in the use of a tetrahydroquinoline derivative compound having the general formula I for the treatment of Graves' associated pretibial dermopathy.

Still another aspect the invention resides in the use of a tetrahydroquinoline derivative compound having the general formula I for the treatment of nodular goitre.

The compounds according to the invention can also be used for the treatment of thyroid cancer.

In another aspect the invention relates to the use of a tetrahydroquinoline derivative compound having the general formula I for the prevention of the here above identified disorders.

The invention is illustrated by the following examples.

EXAMPLES

General Comments

The following abbreviations are used in the examples: DMA=N,N-dimethylaniline, DIPEA=N,N-diisopropylethylamine; TFA=trifluoroacetic acid, DtBAD=di-tert-butyl azodicarboxylate; TBTU=O-Benzotriazole-1-yl-N,N,N',N'-tetramethyluronium tetrafluoroborate; HATU=O-(7-azabenzotriazole-1-yl)-N,N,N',N'-tetramethyluronium hexafluorophosphate; Fmoc=9-fluorenylmethoxycarbonyl; Fmoc-Cl=9-fluorenylmethoxycarbonylchloride; DMF=N,N-dimethylformamide; Boc=tert-butoxycarbonyl; THF=tetrahydrofuran; DMAP=dimethyl-pyridin-4-yl-amine; HOAc=acetic acid; Et$_3$N=triethyl amine; EtOAc=ethyl acetate; DCM=dichloro methane; MeOH=methanol; MeI=methyl iodide; DME=1,2-dimethoxy ethane.

The names of the final products described in the examples are generated using the Beilstein Autonom program (version: 4.01.304).

Unless stated otherwise, all final products of the examples below are lyophilized from water/1,4-dioxane mixtures or water/acetonitrile mixtures. If the compound was prepared as a HCl- or TFA salt, the respective acids were added in appropriate amounts to the solvent mixture before lyophilization.

Example 1

Hexanoic acid (1-acetyl-2,2,4-trimethyl-4-phenyl-1, 2,3,4-tetrahydro-quinolin-6-yl)-amide (a) (2,2,4-Trimethyl-1,2-dihydro-quinolin-6-yl)-carbamic acid tert-butyl ester To a stirred solution of N-boc-1,4-phenylene diamine (13.33 g, 63.9mmol) in mesityl oxide (40ml, 367mmol), under an N$_2$ atmosphere, was added iodine (3.47 g, 12.8 mmol) portionwise over 5minutes. The reaction was stirred at 100° C. for 3 hours, then cooled to ambient temperature and reduced to yield the title compound as a crude brown oil (18.4 g, 100%). The product was used without further purification.

(b) (1-Acetyl-2,2,4-trimethyl-1,2-dihydro-quinolin-6-yl)-carbamic acid tert-butyl ester A stirred solution of the compound described in example 1 (a) (16.4 g, 57 mmol) in THF (200 ml) and pyridine (5.07 ml, 63 mmol), under an N$_2$ atmosphere, was cooled to 0° C. (ice/water bath). Acetylchloride (4.46 ml, 63 mmol) in THF (50 ml) was then added dropwise over a period of 15 minutes. The cooling was removed and the reaction mixture was allowed to warm slowly to ambient temperature and stirred for 3 hours. The reaction was then quenched with water. The organics were extracted with EtOAc, washed with water, dried (Na$_2$SO$_4$), filtered and reduced to an oil. The oil was purified by flash chromatography (heptane/EtOAc 8:2) to yield the title compound (11.95 g, 57%).

(c) 1-(6-Amino-2,2,4-trimethyl-2H-quinolin-1-yl)-ethanone

A stirred solution of the compound described in example 1 (b) (11.95 g, 36 mmol) in DCM (250 ml), under an N$_2$ atmosphere, was cooled to 0° C. (ice/water bath). Trifluoroacetic acid (27.7 ml, 360 mmol) was then added dropwise over a period of 15 minutes. The cooling was removed and the reaction mixture was allowed to warm slowly to ambient temperature and stirred for 1 hour. The reaction was then quenched by the addition of sodium carbonate (s) under vigorous stirring and water was added. The organics were extracted with EtOAc, washed with water, dried (Na$_2$SO$_4$), filtered and reduced to an oil. The oil was purified by flash chromatography (heptane/EtOAc 6:4) to yield the title compound (2.67 g, 32%).

(d) 1-(6-Amino-2,2,4-trimethyl-4-phenyl-3,4-dihydro-2H-quinolin-1-yl)-ethanone

A stirred solution of the compound described in example 1 (c) (100 mg, 494 μmol) in dry benzene (2 ml), under an N$_2$ atmosphere, was cooled to 0° C. (ice/water bath). Aluminium trichloride (198 mg, 1.48 mmol) was then added portionwise over 15 minutes. The cooling was removed and the reaction mixture was allowed to warm slowly to ambient temperature and stirred for 16 hours. The reaction was then quenched with aqueous ammonium chloride. The organics were extracted with EtOAc, washed with water, dried (Na$_2$SO$_4$), filtered and reduced to yield the title compound as a crude brown foam (124 mg, 81%). Product foam was used without further purification.

(e) Hexanoic acid (1-acetyl-2,2,4-trimethyl-4-phenyl-1,2,3,4-tetrahydro-quinolin-6-yl)-amide A stirred solution of the compound described in example 1 (d) (880 mg, 2.85 mmol) and triethylamine (477 µL, 3.42 mmol) in dry DCM (7.5 ml)), under an $N_2$ atmosphere, was cooled to 0° C. (ice/water bath). A solution of hexanoyl chloride (479 µL, 3.42 mmol) in DCM (2.5 ml) was then added drop wise over 15 minutes. The cooling was removed and the reaction mixture was allowed to warm slowly to ambient temperature and stirred for 1 hour. The reaction was then quenched with 1N aqueous hydrochloric acid. The organics were extracted with DCM, washed with $NaHCO_3$ in $H_2O$ solution, then water, then dried (PE filter) and reduced to yield an oil. The oil was purified by flash chromatography then the product crystallized from EtOAc to yield the title compound as a white solid (871 mg, 75%). Data: (m/z)=407.3 $(M+H)^+$.

Example 2

1-Methyl-1H-pyrrole-2-carboxylic acid (1-acetyl-2,2,4-trimethyl-4-phenyl-1,2,3,4-tetrahydro-quinolin-6-yl)-amide DIPEA (70.6 µL, 405 µmol), HATU (46.2 µL, 122 µmol) and N-methylpyrrole-2-carboxylic acid (15.2 mg, 122 µmol) in dry DCM (0.75 ml) were stirred together, under an $N_2$ atmosphere, for 15 minutes. The reaction mixture was then cooled to 0° C. (ice/water bath) then a solution of the compound described in example 1(d) (25 mg, 81.1 µmol) in dry DCM (0.25 ml) was added dropwise over 3 minutes. The cooling was removed and the reaction mixture was allowed to warm slowly to ambient temperature and stirred for 1 hour. The reaction was then quenched with 1N aqueous hydrochloric acid. The organics were extracted with DCM, washed with $NaHCO_3$ in $H_2O$ solution, then water, then dried (PE filter) and reduced to yield an oil. The oil was purified by flash chromatography to yield the title compound as a white solid (15 mg, 46%). Data: (m/z)=416.3 $(M+H)^+$.

Example 3

N-(1-Acetyl-2,2,4-trimethyl-4-phenyl-1,2,3,4-tetrahydro-quinolin-6-yl)-5-bromo-2-methylamino-benzamide This compound was prepared, in an analogous manner as described in Example 2, from the compound described in example 1 (d) (264 mg, 78%) Data: (m/z)=521 $(M+H)^+$.

Example 4

Pyridine-2-carboxylic acid (1-acetyl-2,2,4-trimethyl-4-phenyl-1,2,3,4-tetrahydro-quinolin-6-yl)-amide This compound was prepared, in an analogous manner as described in Example 2, from the compound described in example 1 (d) (320 mg, 46%) Data: (m/z)=414 $(M+H)^+$.

Example 5

N-(1-Acetyl-2,2,4-trimethyl-4-phenyl-1,2,3,4-tetrahydro-quinolin-6-yl)-3,4-dimethyl-benzamide This compound was prepared, in an analogous manner as described in Example 1, from the compound described in example 1 (d), to yield the title compound (320 mg, 46%) Data: (m/z)=414 $(M+H)^+$.

Example 6

(1-Acetyl-2,2,4-trimethyl-4-phenyl-1,2,3,4-tetrahydro-quinolin-6-yl)-carbamic acid 2-phenoxy-ethyl ester To a stirred solution of the compound described in example 1 (d) (124 mg, 402 µmol) and a catalytic amount of activated charcoal in dry EtOAc (4.6 ml), under an $N_2$ atmosphere, was added trichloromethyl chloroformate (97 µl, 804 µmol). The reaction was stirred at reflux for 2 hours, then cooled to ambient temperature and filtered over dikalite and concentrated under reduced pressure to yield the isocyanate as a crude oil (134 mg, 100%).

The isocyanate (48.8 mg, 146 µmol) in THF (1 ml) was then added to a solution of 2-phenoxyethanol (182 µl, 1.46 mmol) and TEA (211 µl, 1.46 mmol) in THF (2 ml), under an $N_2$ atmosphere. The reaction was stirred for 15 hours at ambient temperature, then quenched with water, extracted with EtOAc, washed with brine, dried ($Na_2SO_4$), filtered and reduced to an oil. The oil was purified by flash chromatography (heptane/EtOAc) to yield the title compound (51 mg, 74%). Data: (m/z)=473.5 $(M+H)^+$.

Example 7

(1-Acetyl-2,2,4-trimethyl-4-phenyl-1,2,3,4-tetrahydro-quinolin-6-yl)-carbamic acid butyl ester A stirred solution of the compound described in example 1 (d) (20 mg, 65 µmol) in DCM (2 ml), under an $N_2$ atmosphere, was cooled to 0° C. (ice/water bath). N-butylchloroformate (16.7 µl, 130 µmol) was added and the cooling was removed and the reaction mixture was allowed to warm slowly to ambient temperature and stirred for 16 hours. The reaction was then quenched with water, extracted with EtOAc, washed with brine, dried ($Na_2SO_4$), filtered and reduced to an oil. The oil was purified by flash chromatography (heptane/EtOAc) to yield the title compound (10 mg, 37%) Data: (m/z)=409.3 $(M+H)^+$.

Example 8

1-(1-Acetyl-2,2,4-trimethyl-4-phenyl-1,2,3,4-tetrahydro-quinolin-6-yl)-3-cyclopentyl-urea A stirred solution of the compound described in example 1 (d) (25 mg, 81.1 µmol) and triethylamine (16.9 µL, 122 µmol) in dry DCM (0.75 ml)), under an $N_2$ atmosphere, was cooled to 0° C. (ice/water bath). A solution of cyclopentyl isocyanate (11.0 mg, 97.3 µmol) in DCM (0.25 ml) was then added dropwise over 3 minutes. The cooling was removed and the reaction mixture was allowed to warm slowly to ambient temperature and stirred for 1 hour. The reaction was quenched with 1N aqueous hydrochloric acid. The organics were extracted with DCM, washed with $NaHCO_3$ in $H_2O$ solution and water, then dried (PE filter) and reduced to yield an oil. The oil was purified by flash chromatography to yield the title compound as a white solid (3 mg, 9%). Data: (m/z)=420.5 $(M+H)^+$.

Example 9

Hexanoic acid [1-acetyl-4-(4-bromo-phenyl)-4-methyl-1,2,3,4-tetrahydro-quinolin-6-yl]-amide (a) (E)-3-(4-Bromo-phenyl)-but-2-enoic acid ethyl ester A solution of potassium tert-butoxide (10.45 g, 90.43 mmol) in THF (250 ml) was stirred under nitrogen atmosphere. A solution of triethyl phosphonoacetate (18.1 ml, 90.43 mmol) in THF (100 ml) was then added and the reaction mixture was stirred for 30 minutes at room temperature. A solution of 1-(4-Bromo-phenyl)-ethanone (6 g, 30.14 mmol) in THF (100 ml) was then added dropwise over 5 minutes. The reaction mixture was heated to reflux. After 3 hours the reaction mixture was cooled to ambient temperature and THF was removed under reduced pressure. The reaction mixture was dissolved in $H_2O$, extracted with EtOAc, washed with $H_2O$ and brine, dried ($Na_2SO_4$) and concentrated under reduced pressure. The crude product was purified by column chromatography on silica (Hept:EtOAc 8:2) to afford the title compound (8.1 g, 99%).

(b) (E)-3-(4-Bromo-phenyl)-but-2-enoic acid

To a stirred solution of the compound described in example 9 (a) (8.16 g, 30.3 mmol) in ethanol (50 ml), 2N aqueous sodium hydroxide (50 ml) was added. The reaction mixture was stirred over night at room temperature. The reaction mixture was cooled and quenched with 2N aqueous hydrochloric acid. The organics were extracted into EtOAc, washed with $H_2O$ and brine, dried ($Na_2SO_4$) and concentrated under reduced pressure to yield the title compound as a white solid (7.42 g, 99%). Product used without further purification.

(c) (E)-3-(4-Bromo-phenyl)-but-2-enoic acid phenylamide

To a stirred solution of the compound described in example 9 (b) (2 g, 8.296 mmol) in $CH_2Cl_2$ (40 ml), under $N_2$ atmosphere, DIPEA (2.89 ml, 16.59 mmol) and o-(7-azabenzotriazol-1-yl)-1,1,3,3-tetramethyluroniumhexafluorophosphate (3.79 g, 9.96 mmol) were added. The reaction mixture was stirred for 30 minutes at room temperature and a solution of aniline (910 µl, 9.96 mmol) in $CH_2Cl_2$ (30 ml) was added dropwise. The reaction mixture was stirred for 3.5 hours and then quenched with 3% aqueous citric acid (100 ml), extracted with $CH_2Cl_2$, washed with $H_2O$, dried ($Na_2SO_4$) and concentrated under reduced pressure. The crude product was purified by column chromatography on silica (Hept:EtOAc 8:2) to afford the title compound (2.48 g, 95%).

(d) 4-(4-Bromo-phenyl)-4-methyl-3,4-dihydro-1H-quinolin-2-one

The compound described in example 9 (c) (2.28 g, 7.2 mmol) was dissolved in concentrated sulfuric acid (20 ml) and stirred for 45 minutes. The reaction mixture was poured into an ice/water mixture and the organics were extracted into $CH_2Cl_2$, washed with aqueous $NaHCO_3$ and $H_2O$, dried ($Na_2SO_4$) and concentrated under reduced pressure. The crude product was purified by column chromatography on silica (Hept: EtOAc 8:2) to afford the title compound as a yellow solid (1.9 g, 83%).

(e) 4-(4-Bromo-phenyl)-4-methyl-1,2,3,4-tetrahydro-quinoline

To a solution of the compound described in example 9 (d) (9.09 g, 28.75 mmol) in toluene (475 ml), under $N_2$ atmosphere, a 2M solution of borane-methyl sulfide complex in toluene (37.4 ml, 74.74 mmol) was added dropwise over 20 minutes. The reaction mixture was heated to reflux for 2 hours, then cooled to ambient temperature, quenched with $H_2O$ and stirred for 50 minutes at room temperature. The organics were extracted into $CH_2Cl_2$, washed with $H_2O$, dried ($Na_2SO_4$) and concentrated under reduced pressure to afford the title compound as an oil (8.6 g, 99%). The product was used without further purification.

(f) 1-[4-(4-Bromo-phenyl)-4-methyl-3,4-dihydro-2H-quinolin-1-yl]-ethanone

To a stirred solution of the compound described in example 9 (e) (8.69 g, 28.75 mmol) in $CH_2Cl_2$ (240 ml), under $N_2$ atmosphere, pyridine (4.64 ml, 57.5 mmol) and acetyl chloride (3.08 ml, 43.13 mmol) were added and stirred at room temperature for 3 hours. The reaction mixture was then poured into ice water. The organics were extracted into $CH_2Cl_2$, washed with $H_2O$, dried ($Na_2SO_4$) and concentrated under reduced pressure to afford the title compound as an oil (9.8 g, 99%). The product was used without further purification.

(g) 1-[4-(4-Bromo-phenyl)-4-methyl-6-nitro-3,4-dihydro-2H-quinolin-1-yl]-ethanone To a stirred solution of the compound described in example 9 (f) (9.8 g, 28.47 mmol) in $CH_2Cl_2$ (210 ml), under $N_2$ atmosphere, acetic anhydride (267 µl, 2.85 mmol) was added. A solution of fuming nitric acid (7.17 ml, 0.17 mol) in $CH_2Cl_2$ (10 ml) was then added dropwise over 15 minutes and the reaction mixture was stirred overnight at room temperature. The reaction mixture was then poured into ice water. The organics were extracted into $CH_2Cl_2$, washed with aqueous $NaHCO_3$ and $H_2O$, dried ($Na_2SO_4$) and concentrated under reduced pressure. The crude product was purified by column chromatography on silica (Hept:EtOAc 9:1) to afford the title compound (7.2 g, 65%).

(h) 1-[6-Amino-4-(4-bromo-phenyl)-4-methyl-3,4-dihydro-2H-quinolin-1-yl]-ethanone A stirred solution of the compound described in example 9 (g) (7.3 g, 18.8 mmol) and acetic acid (10.73 ml, 187.6 mmol) in THF (690 ml), under $N_2$ atmosphere, was cooled to 0° C. (ice/water bath). Zinc (dust) (38.1 g, 0.56 mol) was then added portion wise over 15 minutes. The reaction mixture was stirred for 30 minutes at 0° C. The cooling was then removed and the reaction mixture was allowed to warm slowly to ambient temperature and stirred for 16 hours. The solids were filtered off and the filtrate was deluded with EtOAc and water. The organic layer was washed with aqueous $NaHCO_3$ and $H_2O$, dried ($Na_2SO_4$) and concentrated under reduced pressure to afford the title compound as an orange oil (6.67 g, 99%). The product was used without further purification.

(i) Hexanoic acid [1-acetyl-4-(4-bromo-phenyl)-4-methyl-1,2,3,4-tetrahydro-quinolin-6-yl]-amide A stirred solution of the compound described in example 9 (h) (7.54 g, 21.0 mmol) and triethylamine (3.52 ml, 25.2 mmol) in $CH_2Cl_2$ (750 ml), under $N_2$ atmosphere, was cooled to 0° C. (ice/water bath). N-hexanoyl chloride (3.54 ml, 25.2 mmol) was then added dropwise over 5 minutes and the reaction mixture was stirred for 1 hour at 0° C. Then the cooling was removed and the reaction mixture was allowed to stir overnight at room temperature. The reaction was then quenched with aqueous $NaHCO_3$. The organics were extracted into $CH_2Cl_2$, washed with $H_2O$, dried ($Na_2SO_4$) and concentrated under reduced pressure. The crude product was purified by column chromatography on silica (Hept:EtOAc 1:1) to afford the title compound as a yellow foam (5.66 g, 59%). Data: (m/z)=457.3/459.3 (M+H)$^+$.

Example 10

N-(1-Acetyl-4-methyl-4-phenyl-1,2,3,4-tetrahydro-quinolin-6-yl)-2-phenoxy-acetamide (a) 1-(6-Amino-4-methyl-4-phenyl-3,4-dihydro-2H-quinolin-1-yl)-ethanone This compound has been prepared in an analogous manner as described for example 9 (h).

(b) N-(1-Acetyl-4-methyl-4-phenyl-1,2,3,4-tetrahydro-quinolin-6-yl)-2-phenoxy-acetamide To a solution of phenoxyacetic acid (19.5 mg, 0.13 mmol) in DCM (1 ml), TBTU (52 mg, 0.16 mmol) and DIPEA (26 μl, 0.15 mmol) were added and the reaction mixture was stirred at room temperature. After 10 minutes a solution of the compound described in example 10 (a) (30 mg, 0.11 mmol) in DCM (1 ml) was added. The reaction mixture was stirred overnight at room temperature. The reaction was quenched with a saturated NaHCO$_3$ solution in H$_2$O and extracted with DCM. The organic layer was dried (Na$_2$—SO$_4$) and concentrated under reduced pressure. The crude product was purified with column chromatography on silica to afford the title compound (36 mg, 81%). Data: (m/z)=415.5 (M+H)$^+$.

Example 11

N-(1-Acetyl-4-methyl-4-phenyl-1,2,3,4-tetrahydro-quinolin-6-yl)-3-(3-chloro-phenyl)-propionamide This compound was prepared, in an analogous manner as described for example 10, from the compound described in example 10 (a), to afford the title compound (15 mg, 32%). Data: (m/z)=447.3 (M+H)$^+$.

Example 12

N-(1-Acetyl-4-methyl-4-phenyl-1,2,3,4-tetrahydro-quinolin-6-yl)-3-thiophen-2-yl-propionamide This compound was prepared, in an analogous manner as described in Example 11, from the compound described in example 10 (a), to afford the title compound (21 mg, 47%) Data: (m/z)=419 (M+H)$^+$.

Example 13

1-(1-Acetyl-4-methyl-4-phenyl-1,2,3,4-tetrahydro-quinolin-6-yl)-3-(4-chloro-benzyl)-urea This compound was prepared, in an analogous manner as described in example 19 (d), from the compound described in example 10 (a), to afford the title compound (55 mg, 87%). Data: (m/z)=448 (M+H)$^+$.

Example 14

Hexanoic acid {1-acetyl-4-[4-(3-fluoro-pyridin-4-yl)-phenyl]-4-methyl-1,2,3,4-tetrahydro-quinolin-6-yl}-amide A stirred solution of the compound described in Example 9 (50 mg, 0.11 mmol), 3-fluoropyridine-4-boronic acid (42 mg, 0.30 mmol), potassium phosphate tribasic heptahydrate (44 mg, 0.13 mmol), bis(triphenylphosphine)palladium(II) chloride (4.6 mg, 6.6 μmol), triphenylarsine (2.3 mg, 7.6 μmol) and H$_2$O (0.5 ml) in dioxane (3 ml), under N$_2$ atmosphere, was heated to reflux for 5 hours. The reaction mixture was then cooled to ambient temperature, quenched with aqueous NaHCO$_3$ and diluted with EtOAc. The organic layer was washed with H$_2$O and brine, dried (Na$_2$SO$_4$) and concentrated under reduced pressure. The crude product was purified by column chromatography on silica, followed by preparative HPLC. Freeze-drying afforded the title compound (10 mg, 19%). Data: (m/z)=474.5 (M+H)$^+$.

Example 15

[4-(1-Acetyl-6-hexanoylamino-4-methyl-1,2,3,4-tetrahydro-quinolin-4-yl)-phenyl]-carbamic acid 3-chloro-benzyl ester (a) Hexanoic acid [1-acetyl-4-(4-amino-phenyl)-4-methyl-1,2,3,4-tetrahydro-quinolin-6-yl]-amide To a stirred solution of the compound described in Example 9 (5.08 g, 11.1 mmol), tris(dibenzylideneacetone)dipalladium(0)chloroform adduct (850 mg, 0.82 mmol), 2,2'-bis(diphenylphosphino)-1,1'-binaphthyl (850 mg, 1.37 mmol) and sodium tert-butoxide (2.13 g, 22.2 mmol) in DME (200 ml), under N$_2$ atmosphere, benzophenone imine (2.8 ml, 16.8 mmol) was added and heated to 80° C. for 16 hours. The reaction mixture was then cooled to ambient temperature, diluded with EtOAc and solids were filtered off. The filtrate was concentrated under reduced pressure and purified by column chromatography on silica (Hept:EtOAc 7:3) to yield an orange solid. To a stirred solution of this orange solid in THF (21 ml), under N$_2$ atmosphere, 2N aqueous hydrochloric acid was added. After 3 hours the reaction mixture was quenched with EtOAc, made basic with 2N aqueous sodium hydroxide, washed with H$_2$O and brine, dried (Na$_2$SO$_4$) and concentrated under reduced pressure to afford the title compound as an orange oil (3.95 g, 90%). The product was used without further purification.

(b) 4-(1-Acetyl-6-hexanoylamino-4-methyl-1,2,3,4-tetrahydro-quinolin-4-yl)-phenyl]-carbamic acid 3-chloro-benzyl ester This compound was prepared, in an analogous manner as described in Example 6, from the compound described in example 15 (a), to afford the title compound (16 mg, 54%). Data: (m/z)=562 (M+H)$^-$.

Example 16

[4-(1-Acetyl-6-hexanoylamino-4-methyl-1,2,3,4-tetrahydro-quinolin-4-yl)-phenyl]-carbamic acid methyl ester This compound was prepared, in an analogous manner as described in Example 6, from the compound described in example 15 (a), to afford the title compound (10 mg, 41%). Data: (m/z)=452 (M+H)$^-$.

Example 17

Cyclopentanecarboxylic acid (1-acetyl-7-dimethylamino-2,2,4-trimethyl-4-phenyl-1,2,3,4-tetrahydro-quinolin-6-yl)-amide (a) (1-Acetyl-2,2,4-trimethyl-4-phenyl-1,2,3,4-tetrahydro-quinolin-6-yl)-carbamic acid 9H-fluoren-9-ylmethyl ester A stirred solution of the compound described in example 1 (d) (2.39 g, 7.75 mmol) and pyridine (660 µL, 8.14 mmol) in dry DCM (15 ml), under an $N_2$ atmosphere, was cooled to 0° C. (ice/water bath). A solution of 9-fluorenylmethyl chloroformate (2.11 g, 8.14 mmol) in dry DCM (10 ml) was then added dropwise over 15 minutes. After 30 minutes the reaction was quenched with $H_2O$. The organics were extracted and reduced to yield an oil. The oil was purified by flash chromatography. The product was crystallised from MeOH/DCM then filtered off to yield the title compound as a yellow solid (3.94 g, 96%).

(b) (1-Acetyl-2,2,4-trimethyl-7-nitro-4-phenyl-1,2,3,4-tetrahydro-quinolin-6-yl)-carbamic acid 9H-fluoren-9-ylmethyl ester To a stirred solution of the compound described in example 17 (a) (3.94 g, 7.42 mmol) in glacial acetic acid (20 ml) and dry DCM (10 ml), under an $N_2$ atmosphere, was charged with concentrated nitric acid (310 µL, 7.42 mmol), dropwise over 3 minutes. Stirred at ambient temperature for 30 minutes then charged with concentrated nitric acid (100 µL, 2.36 mmol). Stirred for 15 minutes at ambient temperature then the reaction was then quenched with $H_2O$. The organics were extracted. MeOH (2 ml) was added to the organics and the DCM was removed by rotary evaporation. The product was crystallised from MeOH/DCM then filtered off to yield the title compound as a yellow solid (2.62 g, 61%).

(c) (1-Acetyl-7-amino-2,2,4-trimethyl-4-phenyl-1,2,3,4-tetrahydro-quinolin-6-yl)-carbamic acid 9H-fluoren-9-ylmethyl ester A stirred solution of the compound described in example 17 (b) (100 mg, 173 µmol) and glacial acetic acid (100 µL, 1.73 mmol) in dry THF (3 ml), under an $N_2$ atmosphere, was cooled to 0° C. (ice/water bath). Zinc dust (227 mg, 3.47 mmol) was added portionwise over 10 minutes. The cooling was removed and the reaction was allowed to warm to ambient temperature and stirred for 2 hours. Fresh glacial acetic acid (100 µL, 1.73 mmol) and zinc dust (227 mg, 3.47 mmol) were added. After 10 minutes the reaction was filtered through decalite. DCM was added. The organics were washed with $NaHCO_3$, brine and dried ($MgSO_4$), filtered and reduced to yield the title compound as an orange oil (95 mg, 100%).

(d) (1-Acetyl-7-dimethylamino-2,2,4-trimethyl-4-phenyl-1,2,3,4-tetrahydro-quinolin-6-yl)-carbamic acid 9H-fluoren-9-ylmethyl ester To a stirred solution of the compound described in example 17 (c) (103 mg, 189 µmol) in methanol (2 ml) and glacial acetic acid (135 µL, 2.36 mmol) was added sodium cyano borohydride (18.8 mg, 302 µmol) then a 37% solution of formaldehyde in water (14 µL, 189 µmol). After 2 hours the reaction was quenched with $NaHCO_3$ and the organics were extracted into EtOAc. The organics were then washed with brine, dried ($MgSO_4$), filtered and reduced to yield the title compound as a red solid (106 mg, 100%).

(e) 1-(6-Amino-7-dimethylamino-2,2,4-trimethyl-4-phenyl-3,4-dihydro-2H-quinolin-1-yl)-ethanone To a stirred solution of the compound described in example 17 (d) (380 mg, 662 µmol) in dry DCM (5 ml) was added piperidine (1 ml). After 2 minutes the reaction mixture was reduced to an oil by rotary evaporation. The oil was purified by flash chromatography to yield the title compound as a pink solid (232 mg, 100%).

Cyclopentanecarboxylic acid (1-acetyl-7-dimethylamino-2,2,4-trimethyl-4-phenyl-1,2,3,4-tetrahydro-quinolin-6-yl)-amide To a stirred solution of HATU (224 mg, 590 µmol) and DIPEA (340 µL, 1.96 mmol) in DCM (5 ml) was added cyclopentane carbonyl chloride (128 µL, 1.18 mmol). Stirred under an $N_2$ atmosphere for 15 minutes then a solution of the compound described in example 17 (e) (138 mg, 393 µmol) in DCM (5 ml) was added dropwise. After 18 hours the reaction was quenched with 0.5N hydrochloric acid. The organics were washed with NaHCO3, H2O then dried (PE-filter) and reduced to yield an oil. The oil was purified by flash chromatography to yield the title compound as a white solid (147 mg, 85%). Data: (m/z)=448.5 $(M+H)^+$.

Example 18

N-(1-Acetyl-7-dimethylamino-4-methyl-4-phenyl-1,2,3,4-tetrahydro-quinolin-6-yl)-3-(4-chloro-phenyl)-propionamide This compound was prepared, in an analogous manner as described in Example 17, from the compound described in example 10a to afford the title compound (14 mg, 46%) Data: (m/z)=490 $(M+H)^-$.

Example 19

1-(1-Acetyl-7-dimethylamino-4-methyl-4-phenyl-1,2,3,4-tetrahydro-quinolin-6-yl)-3-(2-methoxy-benzyl)-urea (a) (1-Acetyl-4-methyl-4-phenyl-1,2,3,4-tetrahydro-quinolin-6-yl)-carbamic acid 9H-fluoren-9-ylmethyl ester This compound was prepared, in an analogous manner as described in example 17 (a), from the compound described in example 10 (a) to afford the title compound (2.2 g, 82%)

(b) (1-Acetyl-4-methyl-7-nitro-4-phenyl-1,2,3,4-tetrahydro-quinolin-6-yl)-carbamic acid 9H-fluoren-9-ylmethyl ester This compound was prepared, in an analogous manner as described in example 17(b), from the compound described in example 19a to afford the title compound (1.1 g, 58%)

(c) 1-(6-Amino-4-methyl-7-nitro-4-phenyl-3,4-dihydro-2H-quinolin-1-yl)-ethanone

To a stirred solution of the compound described in example 19 (b) (112 mg, 0.2 mmol) in $CH_2Cl_2$ (2 ml), piperidine (0.2 ml, 2 mmol) was added. The reaction was stirred overnight at room temperature. The reaction mixture was poured into H$_2$O and extracted into CH$_2$Cl$_2$. The organics were washed with H$_2$O and brine, dried (Na$_2$SO$_4$) and concentrated under reduced pressure. The product was purified by column chromatography on silica to give the title compound (50 mg, 76%) Data: (m/z)=326 (M+H)$^+$.

(d) 1-(1-Acetyl-4-methyl-7-nitro-4-phenyl-1,2,3,4-tetrahydro-quinolin-6-yl)-3-(2-methoxy-benzyl)-urea To a stirred solution of the compound described in example 19 (c) (20 mg, 61.5 µmol) in EtOAc (3 ml), a cat. amount of activated carbon and diphosgene (15 µl, 123 µmol) were added. The reaction was heated under reflux for 4 hours then filtered over decalite and concentrated under reduced pressure. The crude isocyanate was dissolved in CH$_2$Cl$_2$ (1 ml) and added to a stirred solution of 2-methoxybenzylamine (16 µl, 123 µmol) and Et$_3$N (17 µl, 123 µmol) in CH$_2$Cl$_2$ (2 ml). The reaction was stirred for 3 days at room temperature. The reaction mixture was quenched with H$_2$O and acidified with 2N HCl. The product was extracted into CH$_2$Cl$_2$, dried and purified by column chromatography on silica to give the title compound (23 mg, 77%). Data: (m/z)=489 (M+H)$^+$.

(e) 1-(1-Acetyl-7-amino-4-methyl-4-phenyl-1,2,3,4-tetrahydro-quinolin-6-yl)-3-(2-methoxy-benzyl)-urea To a stirred solution of the compound described in example 19 (d) (23 mg, 47 µmol) in dry THF (2 ml), HOAc (27 µl, 470 µmol) and zinc (62 mg, 940 µmol) were added. The reaction was stirred at room temperature for 3 hours. The reaction mixture was filtered over decalite and poured into H$_2$O. The product was extracted into EtOAc. The organics were washed with aqueous NaHCO$_3$ and brine, dried (Na$_2$SO$_4$) and concentrated under reduced pressure to give the title compound (22 mg, 100%). Data: (m/z)=459 (M+H)$^+$.

(f) 1-(1-Acetyl-7-dimethylamino-4-methyl-4-phenyl-1,2,3,4-tetrahydro-quinolin-6-yl)-3-(2-methoxy-benzyl)-urea To a stirred solution of the crude compound described in example 19 (e) (22 mg, 47 µmol), in MeOH (3 ml) and HOAc (30 µl, 588 µmol), formaldehyde (37% in H$_2$O, (8 µl, 94 µmol)) and NaCNBH$_3$ (6 mg, 94 µmol) were added. The reaction was stirred overnight at room temperature. The reaction mixture was poured into H$_2$O and extracted into EtOAc. The organics were washed with brine, dried (Na$_2$SO$_4$) and concentrated under reduced pressure. The product was purified by column chromatography on silica to give the title compound (15.7 mg, 69%) Data: (m/z)=487(M+H)$^+$.

Example 20

(1-Acetyl-7-dimethylamino-4-methyl-4-phenyl-1,2,3,4-tetrahydro-quinolin-6-yl)-carbamic acid thiophen-2-ylmethyl ester This compound was prepared, in an analogous manner as described in Example 19, from the compound described in example 19 (c) using 2-thiophenemethanol in the first step to afford the title compound (12 mg, 56%) Data: (m/z)=464(M+H)$^+$.

Example 21

Biphenyl-4-carboxylic acid (1-acetyl-7-methoxy-2,2,4-trimethyl-4-phenyl-1,2,3,4-tetrahydro-quinolin-6-yl)-amide

(a) (2-Methoxy-4-nitro-phenyl)-carbamic acid 9H-fluoren-9-ylmethyl ester 2-methoxy-4-nitroaniline (3 g, 17.8 mmol) was dissolved in THF (60 ml) and pyridine (1.6 ml, 19.6 mmol) was added. The reaction mixture was cooled to 0° C. and Fmoc-Cl (5.07 g, 19.6 mmol) was added in small portions. The reaction was allowed to come to ambient temperature and held for 5 hours. The reaction mixture was concentrated under reduced pressure. The crude product was purified by recrystallisation from CH$_2$Cl$_2$ and MeOH to afford the title compound (6.08 g, 88%). Data: (m/z)=391 (M+H)$^+$.

(b) (4-Amino-2-methoxy-phenyl)-carbamic acid 9H-fluoren-9-ylmethyl ester

The compound described in example 21(a) (64.8 g, 0.17 mol) was dissolved in THF (1.5 l) and acetic acid (95 ml, 1.7 mol) was added. The reaction mixture was cooled to 0° C. and zinc (217.1 g, 3.4 mol) was added in small portions. The reaction was allowed to come to ambient temperature and held for 0.5 hour. The reaction mixture was filtered over decalite and the filtrate was washed with a saturated NaHCO$_3$ solution in H$_2$O (2×) and brine (1×), dried (MgSO$_4$) and concentrated under reduced pressure. The crude product was purified by recrystallisation from CH$_2$Cl$_2$ and MeOH to afford the title compound (55.6 g, 93%). Data: (m/z)=361 (M+H)$^+$.

(c) (7-Methoxy-2,2,4-trimethyl-1,2-dihydro-quinolin-6-yl)-carbamic acid 9H-fluoren-9-ylmethyl ester The compound described in example 21(b) (4.45 g, 12.4 mmol), I$_2$ (157 mg, 0.62 mmol), MgSO$_4$ (7.4 g, 62 mmol) and catechol (61 mg, 0.37 mmol) were dissolved/suspended in acetone (350 ml). The reaction mixture was heated to reflux and held for 5 h. The reaction was cooled to ambient temperature and filtered over decalite. The filtrate was concentrated under reduced pressure. The crude product was purified by column chromatography on silica to afford the title compound (4.24 g, 78%). Data: (m/z)=441 (M+H)$^+$.

(d) (1-Acetyl-7-methoxy-2,2,4-trimethyl-1,2-dihydro-quinolin-6-yl)-carbamic acid 9H-fluoren-9-ylmethyl ester The compound described in example 21 (c) (4.24 g, 9.5 mmol) was dissolved in CH$_2$Cl$_2$ (25 ml). First pyridine (25 ml) and a catalytic amount of DMAP were added, and then a solution of acetylchloride (2.0 ml, 28.5 mmol) in CH$_2$Cl$_2$ (20 ml) was added dropwise. The reaction mixture was held at ambient temperature for 15 minutes. The reaction mixture was diluted with CH$_2$Cl$_2$ and extracted with H$_2$O (3×), 0.1 M HCl in H$_2$O (3×), 0.5 M HCl in H$_2$O (1×), dried (MgSO$_4$) and concentrated under reduced pressure. The crude product was purified by column chromatography on silica to afford the title compound (3.91 g, 85%). Data: (m/z)=483 (M+H)$^+$.

(e) 1-(6-Amino-7-methoxy-2,2,4-trimethyl-2H-quinolin-1-yl)-ethanone

The compound described in example 21 (d) (236 mg, 0.49 mmol), was dissolved in CH$_2$Cl$_2$ (4 ml). Piperidine (485 µl, 4.9 mmol) was added and the reaction mixture was held at ambient temperature for 1 hour. The reaction mixture was concentrated under reduced pressure and coevapporated with toluene (2×). The crude product was purified by column chromatography on silica to afford the title compound (90 mg, 71%). Data: (m/z)=261 (M+H)$^+$.

(f) Biphenyl-4-carboxylic acid (1-acetyl-7-methoxy-2,2,4-trimethyl-1,2-dihydro-quinolin-6-yl)-amide The compound described in example 21 (e) (2.22 g, 8.5 mmol) was dissolved in toluene (48 ml) and pyridine (2 ml). 4-biphenylcarbonylchloride (2.21 g, 10.2 mmol) was added and the reaction was held at ambient temperature for 3 hours. An extra equivalent of 4-biphenylcarbonylchloride was added and the reaction was held at ambient temperature for 1 hour. The reaction mixture was concentrated under reduced pressure and coevapporated with toluene (2×). The residue was taken up in EtOAc and extracted with a saturated NaHCO$_3$ solution in H$_2$O, H$_2$O and a 1 M HCl solution in H$_2$O, dried (MgSO$_4$) and concentrated under reduced pressure. The crude product was purified by recrystallisation from CH$_2$Cl$_2$ and MeOH to afford the title compound (3.1 g, 82%). Data: (m/z)=441 (M+H)$^+$.

(g) Biphenyl-4-carboxylic acid (1-acetyl-7-hydroxy-2,2,4-trimethyl-4-phenyl-1,2,3,4-tetrahydro-quinolin-6-yl)-amide The compound described in example 21 (f) (3.1 g, 7.05 mmol) was dissolved in benzene (100 ml). AlCl$_3$ (5.6 g, 42.3 mmol) was added and the reaction was held at ambient temperature for 20 hours. The reaction was quenched with H$_2$O and the reaction mixture was brought to pH 8 by addition of a 2 M NaOH solution in H$_2$O (63 ml) and extracted. The organics were washed with H$_2$O and brine, dried (MgSO$_4$) and concentrated under reduced pressure. The crude product was purified by recrystallisation from acetonitril to afford the title compound (195 mg, 5%). Data: (m/z)=505 (M+H)$^+$.

Biphenyl-4-carboxylic acid (1-acetyl-7-methoxy-2,2,4-trimethyl-4-phenyl-1,2,3,4-tetrahydro-quinolin-6-yl)-amide The compound described in example 21 (g) (600 mg, 1.2 mmol) was dissolved in acetonitril (50 ml). K$_2$CO$_3$ (821 mg, 5.9 mmol) was added and the reaction mixture was heated to 45° C. and held for 15 minutes. MeI (84 µl, 1.3 mmol) was added and the reaction mixture was held at 45° C. for 3 hours. An extra 0.2 equivalents of MeI were added and the reaction was completed in 0.5 hour. The reaction mixture was concentrated under reduced pressure, taken up in EtOAc and washed with H$_2$O and brine, dried (MgSO$_4$) and concentrated under reduced pressure. The crude product was purified by recrystallisation from heptane/EtOAc to afford the title compound (351 mg, 56%). Data: (m/z)=519 (M+H)$^+$.

Example 22

Furan-2-carboxylic acid [1-acetyl-7-methoxy-4-(4-methoxy-phenyl)-2,2,4-trimethyl-1,2,3,4-tetrahydro-quinolin-6-yl]-amide (a) Furan-2-carboxylic acid (1-acetyl-7-methoxy-2,2,4-trimethyl-1,2-dihydro-quinolin-6-yl)-amide The compound described in example 21 (e) (406 mg, 1.56 mmol) was dissolved in CH$_2$—Cl$_2$ (5 ml). 2-furancarbonyl-chloride (170 µl, 1.72 mmol) and DIPEA (815 µl, 4.68 mmol) were added and the reaction mixture was held at ambient temperature for 15 hours. The reaction was quenched with H$_2$O and extracted. The organics were concentrated under reduced pressure and the crude product was purified by column chromatography on silica to afford the title compound (370 mg, 67%). Data: (m/z)=355 (M+H)$^-$.

Furan-2-carboxylic acid [1-acetyl-7-methoxy-4-(4-methoxy-phenyl)-2,2,4-trimethyl-1,2,3,4-tetrahydro-quinolin-6-yl]-amide The compound described in example 22 (a) (260 mg, 0.73 mmol) and AlCl$_3$ (catalytic amount) were dissolved in anisol (5 ml) and held at ambient temperature for 15 hours. The reaction mixture was extracted with H$_2$O and EtOAc. The crude product was purified by column chromatography on silica to afford the title compound (301 mg, 89%). Data: (m/z)=463 (M+H)$^+$.

Example 23

Biphenyl-4-carboxylic acid [1-acetyl-4-(4-cyanomethoxy-phenyl)-2,2,4-trimethyl-1,2,3,4-tetrahydro-quinolin-6-yl]-amide (a) Biphenyl-4-carboxylic acid [1-acetyl-4-(4-methoxy-phenyl)-2,2,4-trimethyl-1,2,3,4-tetrahydro-quinolin-6-yl]-amide This compound was prepared, in an analogous manner as described in Example 22, from the compound described in example 1c to afford the title compound (466 mg, 60%). Data: (m/z)=519 (M+H)$^+$.

(b) Biphenyl-4-carboxylic acid [1-acetyl-4-(4-hydroxy-phenyl)-2,2,4-trimethyl-1,2,3,4-tetrahydro-quinolin-6-yl]-amide The compound described in example 23 (a) (466 mg, 0.9 mmol) was dissolved in CH$_2$—Cl$_2$ (7 ml) and the reaction mixture was cooled to 0° C. BBr$_3$ (680 mg, 2.7 mmol) was added and the reaction was allowed to come to ambient temperature and held for 3 hours. The reaction mixture was cooled to 0° C. and slowly was added a 1 M NaOH solution in H$_2$O and EtOAc. This mixture was acidified and extracted. The organics were dried (MgSO$_4$) and concentrated under reduced pressure. The crude product was purified by column chromatography on silica to afford the title compound (125 mg, 28%). Data: (m/z)=505 (M+H)$^+$.

Biphenyl-4-carboxylic acid [1-acetyl-4-(4-cyanomethoxy-phenyl)-2,2,4-trimethyl-1,2,3,4-tetrahydro-quinolin-6-yl]-amide The compound described in example 23 (b) (118 mg, 0.2 mmol) was dissolved in DMF (5 ml). CsCO$_3$ (325 mg, 0.84 mmol) and (2-chloro-ethyl)-diethyl-amine hydrochloride (43.3 mg, 0.25 mmol) were added and the reaction mixture was held at ambient temperature for 15 hours. The reaction was quenched with water and extracted with EtOAc. The organics were dried (MgSO$_4$) and concentrated under reduced pressure. The crude product was purified by preparative HPLC to afford the title compound (61 mg, 51%). Data: (m/z)=596 (M+H)$^-$.

Example 24

Biphenyl-4-carboxylic acid {1-acetyl-2,2,4-trimethyl-4-[4-(pyridin-4-ylmethoxy)-phenyl]-1,2,3,4-tetrahydro-quinolin-6-yl}-amide This compound was prepared, in an analogous manner as described in Example 23, from the compound described in example 23 (b) to afford the title compound (320 mg, 46%). Data: (m/z)=414 (M+H)⁺.

Example 25

[4-(1-Acetyl-6-hexanoylamino-4-methyl-1,2,3,4-tetrahydro-quinolin-4-yl)-phenyl]-carbamic acid furan-2-ylmethyl ester This compound was prepared, in an analogous manner as described in Example 6, from the compound described in example 15 (a), to afford the title compound (13 mg, 47%). Data: (m/z)=518 (M+H)⁻.

Example 26

N-(1-Acetyl-2,2,4-trimethyl-4-phenyl-1,2,3,4-tetrahydro-quinolin-6-yl)-3-(3-chloro-phenyl)-propionamide This compound was prepared, in an analogous manner as described in Example 2, from the compound described in example 1(d) (12 mg, 4%) Data: (m/z)=475 (M+H).

Example 27

(1-Acetyl-4-methyl-4-phenyl-1,2,3,4-tetrahydro-quinolin-6-yl)-carbamic acid 3-methyl-butyl ester To a stirred solution of the compound described in example 10 (a) (124 mg, 402 µmol) and a catalytic amount of activated charcoal in dry EtOAc (4.6 ml), under an N₂ atmosphere, was added trichloromethyl chloroformate (97 µl, 804 µmol). The reaction was stirred at reflux for 2 hours, then cooled to ambient temperature and filtered over dikalite and concentrated under reduced pressure to yield a crude oil (134 mg, 100%). This oil (20 mg, 0.065 mmol) was dissolved in THF (1 ml) and added to a solution of 3-methyl-1-butanol (70.8 µl, 0.65 mmol) and TEA (94 µl, 0.65 mmol) in THF (2 ml), under a N₂ atmosphere. The reaction was stirred overnight at ambient temperature, then quenched with water, extracted with EtOAc, washed with brine, dried (Na₂SO₄), filtered and reduced to an oil. The oil was purified by flash chromatography (heptane/EtOAc) to yield the title compound (10.9 mg, 42.5%). Data: (m/z)=395 (M+H).

Example 28

(1-Acetyl-4-methyl-4-phenyl-1,2,3,4-tetrahydro-quinolin-6-yl)-carbamic acid 1-methyl-cyclopropylmethyl ester This compound has been prepared in an analogous manner as described for example 27, using 1-methyl cyclopropane methanol (19.1 mg, 68%). Data: (m/z)=393 (M+H).

Example 29

(1-Acetyl-4-methyl-4-phenyl-1,2,3,4-tetrahydro-quinolin-6-yl)-carbamic acid cyclobutylmethyl ester This compound has been prepared in an analogous manner as described for example 27, using cyclobutane methanol (11 mg, 40%). Data: (m/z)=393 (M+H).

Example 30

(1-Acetyl-4-methyl-4-phenyl-1,2,3,4-tetrahydro-quinolin-6-yl)-carbamic acid (R)-1,2-dimethyl-propyl ester This compound has been prepared in an analogous manner as described for example 27, using (R)-(−)-3-methyl-2-butanol (6 mg, 2%). Data: (m/z)=395 (M+H).

Example 31

(1-Acetyl-4-methyl-4-phenyl-1,2,3,4-tetrahydro-quinolin-6-yl)-carbamic acid (1R,2S,4S)-bicyclo[2.2.1]hept-2-yl ester This compound has been prepared in an analogous manner as described for example 27, using endo-norborneol (8 mg, 27%). Data: (m/z)=419 (M+H).

Example 32

(1-Acetyl-4-methyl-4-phenyl-1,2,3,4,4a,8a-hexahydro-quinolin-6-yl)-carbamic acid cyclopentyl ester This compound has been prepared in an analogous manner as described for example 27, using pentenol (46%). Data: (m/z)=393 (M+H).

Example 33

N-(1-Acetyl-4-methyl-4-phenyl-1,2,3,4-tetrahydro-quinolin-6-yl)-3-(3-trifluoromethyl-phenyl)-propionamide This compound was prepared, in an analogous manner as described for example 10, from the compound described in example 10 (a), to afford the title compound (35%). Data: (m/z)=481 (M+H)⁺.

Example 34

(1-Acetyl-4-methyl-4-phenyl-1,2,3,4-tetrahydro-quinolin-6-yl)-carbamic acid 3-chloro-4-fluoro-benzyl ester This compound has been prepared in an analogous manner as described for example 27, using (3-chloro-4-fluoro-phenyl)-methanol (73.3%). Data: (m/z)=467 (M+H).

Example 35

5-Bromo-thiophene-2-carboxylic acid (1-acetyl-4-methyl-4-phenyl-1,2,3,4-tetrahydro-quinolin-6-yl)-amide This compound has been prepared in an analogous manner as described for example 10, using 5-bromo-thiophene-2-carboxylic acid (66%). Data: (m/z)=470 (M+H).

Example 36

(+)-1-(1-Acetyl-4-methyl-4-phenyl-1,2,3,4-tetrahydro-quinolin-6-yl)-3-(4-chloro-benzyl)-urea This compound has been obtained starting from example 13, via chiral HPLC. Column AD-H (5μ) 25×0.46 cm. Eluens: heptane/iso-propyl alcohol 90/10. Retention time: 26.8 min. $[\alpha]_D^{20}=+243°$ (ethyl alcohol, 5 mg/ml)

Example 37

(+)-N-(1-Acetyl-2,2,4-trimethyl-4-phenyl-1,2,3,4-tetrahydro-quinolin-6-yl)-3-(3-chloro-phenyl)-propionamide This compound has been obtained starting from example 26, via chiral HPLC. Column AD-H (5μ) 25×0.46 cm. Eluens: heptane/iso-propyl alcohol 80/20. Retention time: 7.0 min. $[\alpha]_D^{20}=+349°$ (ethyl alcohol, 5 mg/ml)

Example 38

(+)-N-(1-Acetyl-4-methyl-4-phenyl-1,2,3,4-tetrahydro-quinolin-6-yl)-3-(3-trifluoromethyl-phenyl)-propionamide This compound has been obtained starting from example 33, via chiral HPLC. Column AD-H (5μ) 25×0.46 cm. Eluens: heptane/iso-propyl alcohol 90/10. Retention time: 26.8 min. $[\alpha]_D^{20}=+229°$ (ethyl alcohol, 5 mg/ml)

Example 39

(+)-(1-Acetyl-4-methyl-4-phenyl-1,2,3,4,4a,8a-hexahydro-quinolin-6-yl)-carbamic acid cyclopentyl ester This compound has been obtained starting from example 32, via chiral HPLC. Column OD-H (5μ) 25×0.46 cm. Eluens: heptane/ethyl alcohol 85/15. Retention time: 6.6 min. $[\alpha]_D^{20}=+278°$ (ethyl alcohol, 5 mg/ml)

Example 40

(+)-(1-Acetyl-4-methyl-4-phenyl-1,2,3,4-tetrahydroquinolin-6-yl)-carbamic acid 3-chloro-4-fluoro-benzyl ester This compound has been obtained starting from example 34, via chiral HPLC. Column OD (10μ) 25×0.46 cm. Eluens: heptane/ethyl alcohol 80/20. Retention time: 8.1 min. $[\alpha]_D^{20}=+236°$ (ethyl alcohol, 5 mg/ml)

Example 41

Antagonist Activity of Compounds Against TSH at the Human TSH Receptor Expressed in CHO Cells Antagonist activity of the compounds against TSH at the human TSH receptor was tested in Chinese Hamster Ovary (CHO) cells stably transfected with a plasmid encoding the human TSH receptor and a second plasmid with a cAMP responsive element (CRE)/promotor directing the expression of a firefly luciferase reporter gene. Binding of bovine TSH to the Gs-coupled TSH receptor will result in an increase of cAMP, which in turn will induce an increased transactivation of the luciferase reporter. Luciferase activity was quantified using a luminescence counter. The cells were incubated with the test compounds (concentration between 0.316 nM and 10 μM) together with 18 nM bovine TSH (which, at this concentration in the absence of test compound, induced 80% of the maximal luciferase stimulation). The $IC_{50}$ (concentration of test compound causing half-maximal (50%) inhibition of the maximally attainable inhibition of the luciferase stimulation by the compound) and efficacy of the compounds were determined using the software program XLfit (Excel version 4.1, ID Business Solutions Limited). The compounds described in the preceding examples all have an $IC_{50}$ of less than $10^{-6}$M. The examples 12, 13, 23, 18, 1, 4, 20, 7, 6, 11, 26, 27, 28, 29, 30, 33, 31, 32, 34, 35, 36, 37, 38, 39 and 40 show $IC_{50}$ lower than 1E-7M.

Example 42

Antagonist Activity of Compounds Against Human TSI at the Human TSH Receptor Expressed in CHO Cells Antagonist activity of three test compounds against human TSI at the human TSH receptor was tested in Chinese Hamster Ovary (CHO) cells (cultured 16 h in the absence of serum prior to the assay) stably expressing the human TSH receptor and a CRE-driven firefly luciferase reporter gene. TSI was partially purified from the serum of a GD patient by filtration over a 0.45 mm filter, protein G-Sepharose column chromatography, dialysis against phosphate-buffered saline and subsequent concentrating on a 10K Amicon filter. It was confirmed that the TSI preparation does not activate luciferase activity in control CHO cells lacking the human TSHR. The cAMP phosphodiesterase inhibitor rolipram was included in the assay medium (10 μM) to augment TSHR-induced CRE-luciferase synthesis, which was quantified using a luminescence counter. The cells were incubated with compound A, B or C (0.316 nM-10 μM) together with 3.16 mg/ml TSI (or bovine TSH at a equieffective concentration of 18 nM). Compound A is hexanoic acid (1-acetyl-2,2,4-trimethyl-4-phenyl-1,2,3,4-tetrahydro-quinolin-6-yl)-amide (see example 1). Compound B is an enantiomer of (1-Acetyl-4-methyl-4-phenyl-1,2,3,4,4a,8a-hexahydro-quinolin-6-yl) -carbamic acid cyclopentyl ester (see example 39). Compound C is an enantiomer of (1-Acetyl-4-methyl-4-phenyl-1,2,3,4-tetrahydroquinolin-6-yl)-carbamic acid 3-chloro-4-fluoro-benzyl ester (see example 40). All 3 compounds are full antagonists and show $IC_{50}$ of less than $10^{-6}$M (Table I).

TABLE I

|  | IC50 (TSI) | IC50 (bTSH) |
| --- | --- | --- |
| Compound A | 88 nM | 368 nM |
| Compound B | 12 nM | 48 nM |
| Compound C | 47 nM | 192 nM |

Example 43

Antagonist Activity of Compounds at Constitutively Active Human TSH Receptors Expressed in CHO Cells Antagonist activity of two compounds was tested in Chinese Hamster Ovary (CHO) cells transiently transfected with a plasmid encoding one of the 5 most prevalent, constitutively active human TSHR mutants (Thr632Ile, Ala623Val, Ile568Thr, Asp619Gly and Asp633Glu) (van Sande et al. (1995) J. Clin. Endocrinol. Metabol. 80, 2577-2585), which have been identified in autonomously functioning thyroid nodules causing hyperthyroidism. The cells were incubated with $10^{-6}$ M of either the compound of example 35 or example 1 in the presence of 10 µM rolipram. Activity of the TSH receptor mutants was quantified using a Packard cAMP Alphascreen assay. Both compounds inhibited constitutive activity of all 5 receptor mutants by >80% at a concentration of $10^{-6}$ M.

What is claimed:

1. A compound selected from the group consisting of
   1) N-(1-Acetyl-4-methyl-4-phenyl-1,2,3,4-tetrahydro-quinolin-6-yl)-2-phenoxy-acetamide, and
   2) N-(1-Acetyl-4-methyl-4-phenyl-1,2,3,4-tetrahydro-quinolin-6-yl)-3-thiophen-2-yl-propionamide.

2. A compound selected from the group consisting of
   1) (1-Acetyl-2,2,4-trimethyl-4-phenyl-1,2,3,4-tetrahydro-quinolin-6-yl)-carbamic acid 2-phenoxy-ethyl ester;
   2) (1-Acetyl-7-dimethylamino-4-methyl-4-phenyl-1,2,3,4-tetrahydro-quinolin-6-yl)-carbamic acid thiophen-2-ylmethyl ester;
   3) (1-Acetyl-4-methyl-4-phenyl-1,2,3,4-tetrahydro-quinolin-6-yl)-carbamic acid 1-methyl-cyclopropylmethyl ester;
   4) (1-Acetyl-4-methyl-4-phenyl-1,2,3,4-tetrahydro-quinolin-6-yl)-carbamic acid cyclobutylmethyl ester;
   5) (1-Acetyl-4-methyl-4-phenyl-1,2,3,4-tetrahydro-quinolin-6-yl)-carbamic acid (1R,2S,4S)-bicyclo[2.2.1]hept-2-yl ester;
   6) (1-Acetyl-4-methyl-4-phenyl-1,2,3,4,4a,8a-hexahydro-quinolin-6-yl)-carbamic acid cyclopentyl ester;
   7) (1-Acetyl-4-methyl-4-phenyl-1,2,3,4-tetrahydro-quinolin-6-yl)-carbamic acid 3-chloro-4-fluoro-benzyl ester;
   8) (+)-(1-Acetyl-4-methyl-4-phenyl-1,2,3,4,4a,8a-hexahydro-quinolin-6-yl)-carbamic acid cyclopentyl ester; and
   9) (+)-(1-Acetyl-4-methyl-4-phenyl-1,2,3,4-tetrahydro-quinolin-6-yl)-carbamic acid 3-chloro-4-fluoro-benzyl ester.

3. A compound selected from the group consisting of
   1) 1-(1-Acetyl-4-methyl-4-phenyl-1,2,3,4-tetrahydro-quinolin-6-yl)-3-(4-chloro-benzyl)-urea;
   2) (+)-1-(1-Acetyl-4-methyl-4-phenyl-1,2,3,4-tetrahydro-quinolin-6-yl)-3-(4-chloro-benzyl)-urea.

4. A compound selected from the group consisting of
   1) Hexanoic acid (1-acetyl-2,2,4-trimethyl-4-phenyl-1,2,3,4-tetrahydro-quinolin-6-yl)-amide;
   2) 1-Methyl-1H-pyrrole-2-carboxylic acid (1-acetyl-2,2,4-trimethyl-4-phenyl-1,2,3,4-tetrahydro quinolin-6-yl)-amide;
   3) Pyridine-2-carboxylic acid (1-acetyl-2,2,4-trimethyl-4-phenyl-1,2,3,4-tetrahydro-quinolin-6-yl)-amide;
   4) N-(1-Acetyl-2,2,4-trimethyl-4-phenyl-1,2,3,4-tetrahydro-quinolin-6-yl)-3,4-dimethyl-benzamide;
   5) (1-Acetyl-2,2,4-trimethyl-4-phenyl-1,2,3,4-tetrahydro-quinolin-6-yl)-carbamic acid butyl ester;
   6) 1-(1-Acetyl-2,2,4-trimethyl-4-phenyl-1,2,3,4-tetrahydro-quinolin-6-yl)-3-cyclopentyl-urea;
   7) Hexanoic acid [1-acetyl-4-(4-bromo-phenyl)-4-methyl-1,2,3,4-tetrahydro-quinolin-6-yl]-amide;
   8) N-(1-Acetyl-4-methyl-4-phenyl-1,2,3,4-tetrahydro-quinolin-6-yl)-3-(3-chloro-phenyl)-propionamide;
   9) Hexanoic acid {1-acetyl-4-[4-(3-fluoro-pyridin-4-yl)-phenyl]-4-methyl-1,2,3,4-tetrahydro-quinolin-6-yl}-amide;
   10) [4-(1-Acetyl-6-hexanoylamino-4-methyl-1,2,3,4-tetrahydro-quinolin-4-yl)-phenyl]-carbamic acid 3-chloro-benzyl ester;
   11) [4-(1-Acetyl-6-hexanoylamino-4-methyl-1,2,3,4-tetrahydro-quinolin-4-yl)-phenyl]-carbamic acid methyl ester;
   12) N-(1-Acetyl-7-dimethylamino-4-methyl-4-phenyl-1,2,3,4-tetrahydro-quinolin-6-yl)-3-(4-chloro-phenyl)-propionamide;
   13) 1-(1-Acetyl-7-dimethylamino-4-methyl-4-phenyl-1,2,3,4-tetrahydro-quinolin-6-yl)-3-(2-methoxy-benzyl)-urea;
   14) Biphenyl-4-carboxylic acid (1-acetyl-7-methoxy-2,2,4-trimethyl-4-phenyl-1,2,3,4-tetrahydro-quinolin-6-yl)-amide;
   15) Furan-2-carboxylic acid [1-acetyl-7-methoxy-4-(4-methoxy-phenyl)-2,2,4-trimethyl-1,2,3,4-tetrahydro-quinolin-6-yl]-amide;
   16) Biphenyl-4-carboxylic acid [1-acetyl-4-(4-cyanomethoxy-phenyl)-2,2,4-trimethyl-1,2,3,4-tetrahydro-quinolin-6-yl]-amide;
   17) Biphenyl-4-carboxylic acid {1-acetyl-2,2,4-trimethyl-4-[4-(pyridin-4-ylmethoxy)-phenyl]-1,2,3,4-tetrahydro-quinolin-6-yl}-amide;
   18) [4-(1-Acetyl-6-hexanoylamino-4-methyl-1,2,3,4-tetrahydro-quinolin-4-yl)-phenyl]-carbamic acid furan-2-ylmethyl ester;
   19) N-(1-Acetyl-2,2,4-trimethyl-4-phenyl-1,2,3,4-tetrahydro-quinolin-6-yl)-3-(3-chloro -phenyl)-propionamide;
   20) (1-Acetyl-4-methyl-4-phenyl-1,2,3,4-tetrahydro-quinolin-6-yl)-carbamic acid 3-methyl-butyl ester;
   21) (1-Acetyl-4-methyl-4-phenyl-1,2,3,4-tetrahydro-quinolin-6-yl)-carbamic acid (R)-1,2-dimethyl-propyl ester;
   22) N-(1-Acetyl-4-methyl-4-phenyl-1,2,3,4-tetrahydro-quinolin-6-yl)-3-(3-trifluoromethyl-phenyl)-propionamide;
   23) 5-Bromo-thiophene-2-carboxylic acid (1-acetyl-4-methyl-4-phenyl-1,2,3,4-tetrahydro-quinolin-6-yl)-amide;
   24) (+)-N-(1-Acetyl-2,2,4-trimethyl-4-phenyl-1,2,3,4-tetrahydro-quinolin-6-yl)-3-(3-chloro-phenyl)-propionamide;
   25) (+)-N-(1-Acetyl-4-methyl-4-phenyl-1,2,3,4-tetrahydro-quinolin-6-yl)-3-(3-trifluoromethyl-phenyl)-propionamide; and
   26) (+)-(1-Acetyl-4-methyl-4-phenyl-1,2,3,4,4a,8a-hexahydro-quinolin-6-yl)-carbamic acid cyclopentyl ester.

* * * * *